United States Patent [19]
Ligon et al.

[11] Patent Number: 5,955,348
[45] Date of Patent: Sep. 21, 1999

[54] GENETICALLY MODIFIED PSEUDOMONAS STRAINS WITH ENHANCED BIOCONTROL ACTIVITY

[75] Inventors: James Madison Ligon, Apex; Nancy R. Torkewitz, Hurdle Mills; Dwight Steven Hill, Cary; Thomas Deane Gaffney, Chapel Hill; Jill Michelle Stafford, Cary, all of N.C.

[73] Assignee: Novartis AG, Basle, Switzerland

[21] Appl. No.: 08/977,306

[22] Filed: Nov. 25, 1997

[51] Int. Cl.$^6$ .............................. C12N 1/20; C12N 15/00; A01N 63/00; C12P 21/06
[52] U.S. Cl. .................................. 435/252.34; 424/93.2; 424/93.4; 424/93.47; 435/69.1; 435/172.3; 435/183; 435/476; 435/477; 800/20.5
[58] Field of Search ............................... 435/183, 172.3, 435/69.1, 477, 476, 252.34; 424/93.47, 93.4, 93.2; 800/20.5

[56] References Cited

U.S. PATENT DOCUMENTS

| | | | |
|---|---|---|---|
| 5,348,742 | 9/1994 | Howell et al. | 424/93.47 |
| 5,496,547 | 3/1996 | Lam et al. | 424/93.47 |

FOREIGN PATENT DOCUMENTS

| | | | |
|---|---|---|---|
| 472494 | 2/1992 | European Pat. Off. | C12N 15/52 |
| WO94/01561 | 1/1994 | WIPO | C12N 15/31 |
| WO95/33818 | 12/1995 | WIPO . | |

OTHER PUBLICATIONS

Corbell et al., "A Global Regulator of Secondary Metabolite Production in *Pseudomonas fluorescens* PF–5", *Journal of Bacteriology*, 177(21): 6230–6236 (1995).

Gaffney et al., "Global Regulation of Expression of Antifungal Factors by a *Pseudomonas fluorescens* Biological Control Strain", *Molecular Plant–Microbe Interactions*, 7(4): 455–463 (1994).

Hrabak et al., "The lemA Gene Required for Pathogenicity of *Pseudomonas syringae* pv. Syringae on Bean Is a Member of a Family of Two–Component Regulators", *J. of Bacteriology*, 174(9): 3011–3020 (1992).

Laville et al., "Global control in *Pseudomonas fluorescens* mediating antibiotic synthesis and suppression of black root rot of tobacco", *Proc. Natl. Acad. Sci.*, 39: 1562–1566 (1992).

Liao et al., "Molecular Characterization of Two Gene Loci Required for Production of the Key Pathogenicity Factor Pectate Lyase in *Pseudomonas viridiflava*", *Molecular Plant–Microbe Interactions*, 7(3): 391–400 (1994).

Pierson et al., "Cloning and Heterologous Expression of the Phenazine Biosynthetic Locus from *Pseudomonas aureofaciens* 30–84", *Molecular Plant–Microbe Interactions*, 5(4): 330–339 (1992).

*Primary Examiner*—James C. Housel
*Assistant Examiner*—Ja-Na Hines
*Attorney, Agent, or Firm*—J. Timothy Meigs

[57] ABSTRACT

Strains of Pseudomonas have been genetically engineered to have enhanced biocontrol properties. The strains of the invention are particularly effective against plant pathogenic fungi such as species of Rhizoctonia and Pythium, because the strains produce enhanced amounts of antifungal metabolites such as pyrrolnitrin that are active against these fungal pathogens. Both the genetically modified biocontrol strains and the antifungal metabolites can be used as active agents for biocontrol compositions.

28 Claims, No Drawings

GENETICALLY MODIFIED PSEUDOMONAS STRAINS WITH ENHANCED BIOCONTROL ACTIVITY

FIELD OF THE INVENTION

The present invention relates to genetically modified strains of Pseudomonas that have improved biocontrol properties. More specifically it relates to strains that are effective against plant pathogenic fungi.

BACKGROUND OF THE INVENTION

It has been recognized that crops grown in some soils are naturally resistant to certain fungal pathogens. Furthermore, soils that are conducive to the development of these diseases can be rendered suppressive or resistant to the pathogen by the addition of small quantities of soil from a suppressive field (Scher and Baker (1980) Phytopathology 70: 412–417). Conversely, suppressive soils can be made conducive to fungal disease susceptibility by autoclaving, indicating that the factors responsible for disease control are biological. Subsequent research has demonstrated that root colonizing bacteria are responsible for this phenomenon, which is known as biological disease control (Cook and Baker (1983), The Nature and Practice of Biological Control of Plant Pathogens; Amer. Phytopathol. Soc., St. Paul, Minn.).

In many cases, the most efficient strains of biological disease controlling bacteria are fluorescent pseudomonads (Weller et al. (1983) Phytopathology, 73: 463–469). These bacteria have also been shown to promote plant growth in the absence of a specific fungal pathogen by the suppression of detrimental rhizosphere microflora present in most soils (Kloepper et al. (1981) Phytopathology 71: 1020–1024). Important plant pathogens that have been effectively controlled by seed inoculation with these bacteria include *Gaemannomyces graminis*, the causative agent of take-all in wheat (Cook et al. (1976) Soil Biol. Biochem 8: 269–273) and Pythium and Rhizoctonia, pathogens that cause damping off of cotton (Howell et al. (1979) Phytopathology 69: 480–482). Rhizoctonia is a particularly problematic plant pathogen for several reasons. First, it is capable of infecting a wide range of crop plants, and second, there are no commercially available chemical fungicides that are effective in controlling the fungus.

Many biological disease controlling Pseudomonas strains produce antibiotics that inhibit the growth of fungal pathogens (Howell et al. (1979) Phytopathology 69:480–482; Howell et al. (1980) Phytopathology 70: 712–715). These antibiotics have been implicated in the control of fungal pathogens in the rhizosphere. For example, Howell et al. (Phytopathology 69: 480–482; 1979) disclose a strain of *Pseudomonas fluorescens* that produces an antibiotic substance antagonistic to *Rhizoctonia solani*. In addition, other strains of *Pseudomonas fluorescens* having enhanced biocontrol activity against plant pathogenic fungi such as Rhizoctonia and Pythium are disclosed in U.S. Pat. Nos. 5,348,742 and 5,496,547, both of which are hereby incorporated by reference in their entireties. Several other past studies have focused on the effects of mutations that result in the inability of the disease control bacterium to synthesize these antibiotics (Kloepper et al. (1981) Phytopathology 71: 1020–1024; Howell et al. (1983) Can. J. Microbiol. 29: 321–324). In these cases, the ability of the organism to control the pathogen is reduced, but not eliminated.

A particularly effective antibiotic against fungal pathogens is pyrrolnitrin, which is biosynthesized from tryptophan (Chang et al. J. Antibiot. 34: 555–566). Pyrrolnitrin is a phenylpyrrole derivative with strong antibiotic activity that has been shown to inhibit a broad range of fungi (Homma et al., Soil Biol. Biochem. 21: 723–728 (1989); Nishida et al., J. Antibiot., ser. A, 18: 211–219 (1965)). Pyrrolnitrin was originally isolated from *Pseudomonas pyrrocinia* (Arima et al, J. Antibiot., ser. A, 18: 201–204 (1965)), but has since been isolated from Myxococcus species, Burkholdaria species, and several other Pseudomonas species such as Ps. FLUORESCENS (Gerth et al. J. Antibiot. 35: 1101–1103 (1982); J. N. Roitman, N. E. Mahoney and W. J. Janisiewicz, Applied Microbiology and Biotechnology 34:381–386 (1990)). The compound has been reported to inhibit fungal respiratory electron transport (Tripathi & Gottlieb, J. Bacteriol. 100: 310–318 (1969)) and uncouple oxidative phosphorylation (Lambowitz & Slayman, J. Bacteriol. 112: 1020–1022 (1972)). It has also been proposed that pyrrolnitrin causes generalized lipoprotein membrane damage (Nose & Arima, J. Antibiot., ser A, 22: 135–143 (1969); Carlone & Scannerini, Mycopahtologia et Mycologia Applicata 53: 111–123 (1974)). U.S. Pat. No. 5,639,949 and U.S. Pat. No. 5,817,502, both of which are hereby incorporated by reference in their entireties, describe the cloning and characterization of the pyrrolnitrin biosynthetic genes from *Ps. fluorescens* and *Ps. pyrrocinia*.

An important factor in biological control is the ability of a biocontrol organism to compete in a given environment (Baker et al. (1982) Biological Control of Plant Pathogens, American Phytopathological Society, St. Paul, Minn., pages 61–106). Thus, it is desirable to obtain strains of biocontrol agents that effectively control the growth of fungal pathogens such as Rhizoctonia and Pythium and that are also able to aggressively compete with indigenous bacteria and microflora existing in the rhizosphere of the plant.

SUMMARY OF THE INVENTION

The present invention is drawn to genetically engineered biocontrol strains of Pseudomonas that are able to effectively control pathogenic attack on crop plants. Preferred biocontrol strains include the following strains of *Pseudomonas fluorescens*, which are described in detail in the examples below: CGA376146, CGA364473, CGA375258, CGA376148, CGA364476, CGA375260, CGA375259, CGA378584, CGA267pPhz, CGA364474, CGA364475, CGA366259, CGA376150, NOA402208, NOA402212, NOA402214, NOA402216, CGA267356/Phl, NOA409068, NOA413174, NOA413175, NOA413176, NOA413177, and NOA413178. The biocontrol strains of the invention produce at least one antifungal substance that is capable of inhibiting a broad spectrum of plant pathogens such as Rhizoctonia and Pythium. In a preferred embodiment, the biocontrol strains of the invention produce enhanced quantities of pyrrolnitrin; see, e.g., Table 1. As shown in Table 2, such strains have increased biocontrol properties and are able to aggressively compete in the plant rhizosphere. The genotypes of the biocontrol strains of the invention are summarized in Table 3 and deposit information for the biocontrol strains of the invention is given in Table 4. The present invention is also intended to encompass pyrrolnitrin producing strains derived from the above-listed strains.

The present invention is also drawn to biocontrol compositions comprising the biocontrol strains of the invention in combination with a chemical fungicide such as a metalaxyl compound. In addition, methods of making the biocontrol strains as well as methods of using the strains and biocontrol compositions for control of pathogenic attack on crops are described.

BRIEF DESCRIPTION OF THE SEQUENCES IN THE SEQUENCE LISTING

SEQ ID NO:1 is the nucleotide sequence of the 11 kb EcoRI fragment containing the gacA gene and derived from the chromosome of Pseudomonas fluorescens strain CGA267356. The coding sequences in this sequence include genes encoding: a methyltransferase (bases 210–1688) with homology to the cheR and frzF genes from E. coli and Myxococcus xanthus, respectively; a sensor kinase (bases 1906–3633) with homology to the rcsC, frzE and bvgS genes of E. coli, M. xanthus, and Borditella pertussis, respectively; a tRNA (bases 4616–4691, complementary DNA strand) with homology to glyW from E. coli; CDP-diacylglycerol-glycerol-3-phosphate-3-phosphatidyltransferase (bases 4731–5318, complementary DNA strand) with homology to pgsA; UVR exonuclease subunit C (bases 5574–7397, complementary DNA strand) with homology to uvrC; and a response regulator/transcription activator (gacA; bases 7400–8041, complementary DNA strand) with homology to the uvrY and GACA genes of E. coli and P. fluorescens, respectively.

SEQ ID NO:2 is the nucleotide sequence of the native gacA regulatory gene.

SEQ ID NO:3 is the protein sequence encoded by the native gacA regulatory gene.

SEQ ID NO:4 is the nucleotide sequence of the ATG-gacA regulatory gene, wherein the first base in the coding sequence has been changed from the native thymidine (T) to an adenine (A) to create the more efficient ATG translation initiation codon.

SEQ ID NO:5 is the protein sequence encoded by the altered ATG-gacA regulatory gene.

SEQ ID NO:6 is the nucleotide sequence of the pyrrolnitrin gene cluster.

SEQ ID NO:7 is the nucleotide sequence of the tac promoter/rrnB transcription terminator cassette.

SEQ ID NO:8 is the nucleotide sequence of the lemA gene.

SEQ ID NO:9 is the nucleotide sequence of the gac*3 regulatory gene, wherein the adenine (A) base at position 395 has been changed from the native adenine (A) to a guanine (G) so that codon 132 encodes an arginine residue instead of the usual glutamine.

SEQ ID NO:10 is the protein sequence encoded by the altered gac*3 regulatory gene.

SEQ ID NO:11 is the nucleotide sequence of the phenazine gene cluster.

DETAILED DESCRIPTION OF THE INVENTION

The present invention provides improved biocontrol strains of Pseudomonas that can be used to control pathogenic attack on crop plants. Such strains are able to aggressively compete in the plant rhizosphere as well as produce one or more antifungal substances that are effective against a broad spectrum of plant pathogenic fungi such as Rhizoctonia and Pythium.

The biocontrol strains of the present invention are important for several reasons. First, Rhizoctonia such as *Rhizoctonia solani* are particularly pernicious plant pathogens. The affected plants include beans, wheat, tomato and potato, in addition to cotton. Second, there are few environmentally safe and effective fungicide treatments available for the protection of crops from Rhizoctonia. Therefore, the use of the disclosed biocontrol strains to control or prevent Rhizoctonia infections in crop plants provides an environmentally safe and effective method of controlling this and other plant pathogens.

Pseudomonas fluorescens strain CGA267356 (also known as both MOCG134 and BL915) has been shown to be effective in controlling plant pathogenic fungi such as Rhizoctonia and Pythium. Strain CGA267356 is one of the subjects of U.S. Pat. No. 5,348,742. Two mutants of CGA267356, strains CGA321730 (a.k.a. MOCG134-8392) and CGA319115, have been constructed and shown to demonstrate even better biological control (biocontrol) of these phytopathogens. CGA321730 and CGA319115 are the subject of U.S. Pat. No. 5,496,547.

Two genes have been isolated from strain CGA267356 that encode proteins that regulate the synthesis of several antifungal compounds produced by the strain, including the antifungal metabolite pyrrolnitrin (prn). These are the lemA gene and gafA (a.k.a. gacA) gene that encode sensor kinase and response regulator proteins, respectively, which function as a typical two-component bacterial regulatory system. These genes and their use to activate biocontrol activity in biocontrol strains are described in U.S. Pat. No. 5,670,350, which is hereby incorporated by reference in its entirety. In addition, U.S. Pat. No. 5,639,949 and U.S. Pat. No. 5,817,502 describe a four gene cluster isolated from strain CGA267356 that encodes proteins that direct the biosynthesis of pyrrolnitrin.

In the present invention, the lemA and gacA regulatory genes and the pyrrolnitrin biosynthetic genes have been utilized to genetically modify parent Ps. fluorescens strain CGA267356 to construct altered strains that demonstrate enhanced production of antifungal metabolites, i.e. pyrrolnitrin, and accordingly enhanced biocontrol activity. In addition, genes from Pseudomonas aureofaciens strain 30-84 that are involved in the synthesis of the antifungal metabolite phenazine-1-carboxylic acid (PCA) have been utilized to genetically modify parent Ps. fluorescens strain CGA267356 to produce PCA, thereby improving the biocontrol activity of strain CGA267356.

A further embodiment of the invention provides a method for controlling or inhibiting the growth of a plant pathogenic fungus by applying the genetically engineered biocontrol strains of the invention to an environment in which the plant pathogenic fungus may grow. This can be to the plant/s or parts of the plant/s (before or after harvest) or to the seeds (prior to planting) of the plant/s to be protected, or alternatively to soil in which the plant/s to be protected are growing or will grow. The biocontrol strains are applied in an effective amount; that is, in an amount sufficient to control or inhibit the pathogen. The rate of application may vary according to the crop to be protected, the efficacy of the biocontrol strain, the pathogen to be controlled, and the severity of the disease pressure. Generally, the rate of application is about $1.3 \times 10^5$ cfu/cm to about $1.3 \times 10^{10}$ cfu/cm, specifically about $1.3 \times 10^6$ cfu/cm to about $1.3 \times 10^9$ cfu/cm, more specifically about $1.3 \times 10^7$ cfu/cm to about $1.3 \times 10^8$ cfu/cm.

A more particular embodiment of the present invention provides methods of inhibiting the growth of Rhizoctonia and Pythium by applying the biocontrol strains of the invention to environments in which the plant pathogenic fungi may grow. This can be to the plant/s or parts of the plant/s (before or after harvest) or to the seeds (prior to planting) of the plant/s to be protected, or alternatively to soil in which the plant/s to be protected are growing or will grow. As noted above, the rate of application varies depending on various factors. However, the general rate of application is about $1.3 \times 10^5$ cfu/cm to about $5 \times 10^9$ cfu/cm, specifically about $1.3 \times 10^6$ cfu/cm to about $1.3 \times 10^9$ cfu/cm more specifically about $1.3 \times 10^7$ cfu/cm to about $1.3 \times 10^8$ cfu/cm.

The recombinant biocontrol strains of the present invention may be used in any manner known in the art, including coating seeds with an effective amount of the biocontrol strains, in furrow application of the biocontrol strains directly into the soil, in foliar application, and in post-harvest disease control. Such methods are well known in the art and are described, for example, in U.S. Pat. No. 5,348,742 and in the published European Application EP 0 472 494 A2, which is hereby incorporated by reference. Furthermore, the strains of this application can also be mixed in formulation with known pesticides in a manner described in WO 94/10845, which disclosure is herein incorporated by reference.

EXAMPLES

The invention is illustrated in further detail by the following detailed procedures, preparations, and examples. The examples are for illustration only, and are not to be construed as limiting the scope of the present invention. Standard recombinant DNA and molecular cloning techniques used here are well known in the art and are described by Sambrook, et al., *Molecular Cloning*, eds., Cold Spring Harbor Laboratory Press, Cold Spring Harbor, N.Y. (1989) and by T. J. Silhavy, M. L. Berman, and L. W. Enquist, *Experiments with Gene Fusions*, Cold Spring Harbor Laboratory, Cold Spring Harbor, N.Y. (1984) and by Ausubel, F. M. et al., *Current Protocols in Molecular Biology*, pub. by Greene Publishing Assoc. and Wiley-Interscience (1987).

Example 1

Construction of Strain CGA376146 (MONO571) (CGA321730, pE11)

Strain CGA376146 (a.k.a. MONO571) was constructed by introducing plasmid pE11 into *P.fluorescens* strain CGA321730 (a.k.a. MOCG-0134-8392) by conjugation. Strain CGA321730 is described in U.S. Pat. No. 5,496,547 and is a transposon mutant of wild-type *P. fluorescens* strain CGA267356 (U.S. Pat. No. 5,348,742) that has enhanced biocontrol activity over the wild-type strain. Strain CGA267356 has been deposited with the ATCC and assigned ATCC accession number 55169. Strain CGA321730 has been deposited with the NRRL and assigned accession number NRRL B-21173. Plasmid pE11 (U.S. Pat. No. 5,670,350) was constructed by ligating the 11 kilobase (kb) EcoRI fragment derived from the chromosome of strain CGA267356 into the broad host range plasmid vector pRK290 (Ditta et al., *Proc. Natl. Acad. Sci. USA* 77:7347–7351 (1980). Plasmid pE11 has been deposited with ATCC and has been assigned ATCC accession number 40869.

The 11-kb EcoRI fragment contains the gacA (gafA) gene that encodes a response regulator protein known to regulate the synthesis of antifungal compounds. This 11-kb EcoRI fragment is described in U.S. Pat. No. 5,670,350 and is set forth herein as SEQ ID NO:1. The plasmid vector, pRK290, used in constructing pE11, is derived from native Pseudomonas plasmids. It is mobilizable but not self-transmissible by conjugation and it carries a tetracycline resistance gene (Ditta et al., 1980).

New strain CGA376146 has been shown to produce higher amounts of the antifungal metabolite pyrrolnitrin (Table 1) and to have higher biocontrol activity (Table 2) compared to the related strains CGA267356 and CGA321730. New strain CGA376146 was deposited with the NRRL on Sep. 5, 1997, and assigned accession no. NRRL B-21811.

Example 2

Construction of Strain CGA364473 (MONO517) (ATG-gacA)

*P. fluorescens* strain CGA364473 (a.k.a. MONO517) was derived from parent *P. fluorescens* strain CGA267356 by changing a single base in the chromosome of the parent strain.

The native gacA regulatory gene begins with the unusual TTG translation initiation codon (SEQ ID NO:2). All proteins in nature are synthesized with methionine as the first amino acid on the amino terminus and ATG is the only codon that encodes methionine. Therefore, the normal translation initiation codon for most genes is ATG. Alternate translation initiation codons GTG and TTG will also result in the incorporation of methionine as the first amino acid since methionine must always be the first amino acid in a newly synthesized protein, but they usually cause a reduction in the efficiency of translation. As a result, fewer protein molecules are made from the same amount of messenger RNA.

To create strain CGA364473, the first base in the coding sequence of the gacA gene was changed from a thymidine (T) to an adenine (A) to create the more efficient ATG translation initiation codon (SEQ ID NO:4). This change was created in vitro by PCR technology and the native gacA gene in the chromosome of strain CGA267356 was replaced with the ATG/gacA gene by homologous gene replacement. The amino acid sequence of the GacA protein encoded by this altered gacA gene (SEQ ID NO:5) is identical to that encoded by the native gene (SEQ ID NO:3), but translation should be more efficient, resulting in synthesis of higher amounts of the protein.

New strain CGA364473 has been shown to produce higher amounts of the antifungal metabolite pyrrolnitrin (Table 1) and to have higher biocontrol activity (Table 2) compared to strain CGA267356. New strain CGA364473 was deposited with the NRRL on Sep. 5, 1997, and assigned accession no. NRRL B-21812.

Example 3

Construction of Strain CGA375258 (MONO568) (pPrn)

Strain CGA375258 (a.k.a. MONO568) was created by introducing plasmid pPrn into the parent *P. fluorescens* strain CGA267356. Plasmid pPrn was constructed by cloning a 6.2 kb XbaI/NotI gene fragment from plasmid pCIB 169 (which was derived from *P. fluorescens* strain CGA267356) into the expression vector pKK223-3, as described in Examples 7–11 of U.S. Pat. No. 5,639,949 and U.S. Pat. No. 5,817,502 (See SEQ ID NO:6). Plasmid pCIB 169 has been deposited with the NRRL and assigned accession number NRRL B-21256. The 6.2 kb XbaI/NotI gene fragment of SEQ ID NO:6 contains the prnABCD gene cluster that encodes genes for the biosynthesis of pyrrolnitrin as described in U.S. Pat. No. 5,639,949 and Ser. No. 08/729,214. A 6.9 kb BglII fragment containing the prnABCD gene cluster with the tac promoter (see SEQ ID NO:7) upstream of the gene cluster and the rrnB transcription terminator (SEQ ID NO:7) derived from plasmid pKK223-3 downstream of the cluster was subsequently cloned into the BglII site of plasmid pRK290 to create plasmid pPrn.

The tac promoter is a small DNA fragment (less than 100 bases) derived from *E. coli*, which is known to be a regulatory element or promoter (Amann, et al, Gene 25:167–178 (1983)) that does not itself encode a protein product. SEQ ID NO:7 presents the sequence of the BssHII DNA fragment containing the tac promoter and the rrnB transcription terminator derived from plasmid pKK223-3. The tac promoter is known to be highly expressed in a constitutive manner in Pseudomonas. Its use with the prn genes causes constitutive, high-level expression of these genes. On the other hand, in the native strain, the promoter for the pyrrolnitrin genes is regulated by the gacA gene product; accordingly, the pyrrolnitrin genes are expressed in the native strain only in the stationary phase of growth.

New strain CGA375258 has been shown to produce higher amounts of the antifungal metabolite pyrrolnitrin (Table 1) and to have higher biocontrol activity (Table 2) compared to the related strain CGA267356. New strain CGA375258 was deposited with the NRRL on Sep. 5, 1997, and assigned accession no. NRRL B-21813.

Example 4

Construction of Strain CGA376148 (MONO573) (CGA321730, pPrn)

The chromosomal background of strain CGA376148 (a.k.a. MONO573) is the same as strain CGA376146 (Example 1). In addition, strain CGA376148 contains the plasmid pPrn (Example 3) that carries the tac promoter fused to the prnABCD gene cluster.

New strain CGA376148 has been shown to produce higher amounts of the antifungal metabolite pyrrolnitrin (Table 1) and to have higher biocontrol activity (Table 2) compared to the related strain CGA267356. New strain CGA376148 was deposited with the NRRL on Sep. 5, 1997, and assigned accession no. NRRL B-21814.

Example 5

Construction of Strain CGA364476 (MONO520) (pLem/Gac)

Strain CGA364476 (a.k.a. MONO520) is the same as wild-type strain CGA267356, except that strain CGA364476 also contains a plasmid with the lemA and gacA genes derived from the chromosome of the wild-type strain CGA267356.

The plasmid containing the lemA and gacA genes, pLem/Gac, was constructed as follows: The plasmid pCIB 146 (Examples 20 and 21 and FIG. 4 of U.S. Pat. No. 5,670,350) contains about 25-kb of chromosomal DNA from strain CGA267356. The lemA gene (see SEQ ID NO:8) has been described and shown to be located in this DNA. The subcloned DNA in pCIB 146 is flanked on each side by NotI and EcoRI sites. An approximately 16-kb HindIII/NotI fragment from pCIB 146, which contains the lemA gene, was excised from pCIB 146. The NotI end was converted to a HindIII site to facilitate cloning of the fragment into the unique HindIII fragment of plasmid pE11 (Example 1), which contains the gacA gene. Insertion of the 16-kb lemA-containing HindIII fragment into the HindIII site of pE11 did not disrupt the function of the gacA gene, because the HindIII site is not within its coding sequence.

New strain CGA364476 has been shown to produce higher amounts of the antifungal metabolite pyrrolnitrin (Table 1) and to have higher biocontrol activity (Table 2) compared to the related strain CGA267356. New strain CGA364476 was deposited with the NRRL on Sep. 5, 1997, and assigned accession no. NRRL B-21815.

Example 6

Construction of Strain CGA375260 (MONO570) (gac*3)

Strain CGA375260 (a.k.a. MONO570) differs from the parent strain CGA267356 by a single base change within the coding sequence of the native gacA gene (SEQ ID NO:2). This modification was generated by introducing the native gacA gene into the hypermutagenic *E. coli* strain XL1-Red (from Stratagene, Inc.). The plasmid was recovered and introduced into a lemA mutant of strain CGA267356 that also contained lacZY genes inserted into an unknown chromosomal gene whose expression is regulated by LemA and GacA. Clones containing randomly mutated gacA genes that resulted in expression of the lacZY genes, as indicated by the formation of blue colonies on agar containing X-Gal, were further analyzed. These clones contained gacA genes that did not require phosphorylation by LemA in order to be active as a transcriptional activator. Three such gacA genes were isolated in this manner and the nucleotide sequence of each was determined. In each, there was a different single base change that resulted in a different single amino acid change in the encoded GacA protein. Each of the three modified gacA genes were used to replace the native gacA gene in strain CGA267356 by perfect site replacement mediated through homologous recombination.

Of the three, only one clone with a LemA-independent gacA gene (gac*3) was shown to have enhanced pyrrolnitrin synthesis and biocontrol activity (Tables 1 and 2). The nucleotide sequence of the gac*3 gene of this clone, CGA375260, was determined (SEQ ID NO:9) and it was found that a single base change occurs in codon 132, which is CAG and encodes a glutamine residue in the native GacA protein. The adenine base in this codon was changed to guanine to create a codon that encodes an arginine residue (CGG) in the altered strain. Therefore, the GacA protein (SEQ ID NO:10) in this strain has an arginine at amino acid 132 instead of the usual glutamine. In all other respects, this strain is identical to the parent strain. In the normal regulatory system and under the proper conditions, the LemA protein phosphorylates GacA and in the phosphorylated state it activates transcription of genes involved in the synthesis of antifungal compounds. This single base change in the GacA protein renders it active irrespective of the kinase activity of the LemA protein.

New strain CGA375260 was deposited with the NRRL on Sep. 5, 1997, and assigned accession no. NRRL B-21816.

Example 7

Construction of Strain CGA375259 (MONO569) (tac/gacA, pPrn)

Strain CGA375259 (a.k.a. MONO569) was derived from strain CGA267356 by replacement of the native promoter controlling expression of the chromosomal gacA gene with the tac promoter from *E. coli* (Example 3) and introduction of plasmid pPrn (Example 3).

The promoter of the gacA gene was replaced with the tac promoter as follows: A unique NruI site in the 2-kb XhoI gacA gene-containing fragment of pCIB 137 (Examples 6 and 7 of U.S. Pat. No. 5,670,350) located 12-bp upstream of the translation start site of the gacA gene was modified by PCR to change it to a BamHI site. Plasmid pCIB 137 has been deposited with the NRRL and assigned accession number NRRL B-18981. A second BamHI site was inserted immediately 5' to the gacA translation start site using PCR. This created a small BamHI fragment immediately preceding the gacA coding sequence. This short BamHI fragment was excised and the DNA was religated to create a new BamHI site. The tac promoter was excised from plasmid pKK223-3 (SEQ ID NO:7) as a BglII/BamHI fragment and cloned in the appropriate orientation into the new BamHI site 5' to the beginning of the gacA gene, which was created by the excision of the above short BamHI fragment. This tac promoter/gacA gene (tac/gacA) fragment was excised as an XhoI fragment and was used to replace the native gacA gene on the 2-kb XhoI site in a plasmid containing the HindIII/EcoRI fragment from pE11. This plasmid was introduced into a gacA deletion mutant of strain CGA267356 (Example 9 of U.S. Pat. No. 5,670,350). Perfect replacement clones were generated (Example 9 of U.S. Pat. No. 5,670,350) and selected by restoration of the wild-type colony morphology. The newly inserted tac/gacA gene resulted in a higher level of expression of the gacA gene, compared to the low level of expression from the native gacA gene promoter.

Plasmid pPrn described in Example 3 above was subsequently introduced into the strain containing the tac/gacA gene to make strain CGA375259.

New strain CGA375259 has been shown to produce higher amounts of the antifungal metabolite pyrrolnitrin (Table 1) and to have higher biocontrol activity (Table 2) compared to the related strain CGA267356. New strain CGA375259 was deposited with the NRRL on Sep. 5, 1997, and assigned accession no. NRRL B-21817.

Example 8

Construction of Strain CGA378584 (MONO591) (cPrn, pLem/Gac)

Strain CGA378584 (a.k.a. MONO591) contains the tac/prnABCD gene cluster described in Example 3 in the chromosome and it also contains plasmid pLem/Gac described in Example 5.

The tac/prnABCD genes were inserted in the chromosome of strain CGA267356 by modification of the E. coli cloning vector pKK223-3 by adding a kanamycin resistance gene derived from plasmid pUC4K (Pharmacea) into the PstI site of the multiple cloning site and by removing the EcoRI, NotI, and BamHI sites of pKK223-3. A 16-kb KpnI gene fragment derived from pCIB 169 (FIG. 4 of U.S. Pat. No. 5,639,949) was cloned into the modified pKK223-3. Plasmid pCIB 169 has been deposited with the NRRL and assigned accession number NRRL B-21256.

The prnABCD genes were deleted by digestion of the plasmid with EcoRI and NotI, conversion of the EcoRI and NotI ends to BamHI by fill-in, linkering, and religation. The 6.9-kb BglII fragment (Example 3), which contains the tac promoter/prnABCD/rrnB terminator construction, was ligated into the BamHI site, thus introducing these modified genes into the plasmid. This plasmid was introduced into strain CGA267356 by conjugation and the native prnABCD gene cluster was replaced with the tac promoter/prnABCD/rrnB terminator construct by homologous recombination.

Plasmid pLem/Gac (Example 5) was introduced into the strain with the chromosomally located tac promoter/prnABCD/rrnB terminator to create strain CGA378584.

New strain CGA378584 has been shown to produce higher amounts of the antifungal metabolite pyrrolnitrin (Table 1) and to have higher biocontrol activity (Table 2) compared to the related strain CGA267356. New strain CGA378584 was deposited with the NRRL on Sep. 5, 1997, and assigned accession no. NRRL B-21818.

Example 9

Construction of Strain CGA267pPhz (MONO597) (pPhz)

This strain is the same as Pseudomonas strain CGA267356, except that strain CGA267pPhz (a.k.a. MONO597) contains a plasmid carrying DNA from Pseudomonas aureofaciens strain 30-84 that contains 5 genes known to encode the pathway for the biosynthesis of the antifungal metabolite phenazine-1-carboxylic acid (PCA).

A 5.7-kb EcoRI/HindIII gene fragment (SEQ ID NO:11) containing the phzFABCD gene cluster from P. aureofaciens (Pierson, et al., FEMS Microbiol. Lett. 134:299–307 (1995)) was ligated into DNA of plasmid pUCP26 (West, et al., Gene 128:81–86 (1994)) that had been restricted with EcoRI and HindIII to create plasmid pPhz. Plasmid pUCP26 is an E. coli/Pseudomonas shuttle plasmid that has a lac promoter flanking the multiple cloning site. The EcoRI and HindIII sites are oriented with the lac promoter such that the EcoRI site is closer to the promoter. Therefore, cloning of the EcoRI/HindIII phzFABCD gene fragment, in which the phz genes are cotranscribed on a single operon oriented in the EcoRI to HindIII direction into plasmid pUCP26, results in the proper juxtaposition of the lac promoter and phz gene cluster to cause expression of these genes from that promoter.

New strain CGA267pPhz has been shown to produce PCA, an antifungal metabolite not normally produced by parent strain CGA267356. It also produces the metabolites normally produced by the parent strain, including pyrrolnitrin. New strain CGA267pPhz was deposited with the NRRL on Sep. 5, 1997, and assigned accession no. NRRL B-21819.

Example 10

Construction of Strain CGA364474 (MONO518) (lac/gacA)

Strain CGA364474 (a.k.a. MONO518) was constructed by juxtaposition of the lac promoter element from E. coli (de Boer et al., Proc. Natl. Acad. Sci. USA 80:21–25 (1983)) with the gacA gene (SEQ ID NO:2) residing in the chromosome of P. fluorescens strain CGA267356 (U.S. Pat. No. 5,348,742) such that expression of the gacA gene is regulated by the lac promoter. The lac promoter is a small DNA fragment that is known to promote gene expression and does not itself encode a protein product. It provides strong, constitutive expression of genes in Pseudomonas. The lac promoter and the gacA gene were fused precisely by overlapping PCR and the lac/gacA promoter/gene DNA fragment replaced the native gacA gene in the chromosome of strain CGA267356 by homologous recombination.

Strain CGA364474 has been shown to produce higher amounts of the antifungal metabolite pyrrolnitrin (Table 1) and to provide higher biocontrol activity (Table 2) than parent strain CGA267356. New strain CGA364474 was deposited with the NRRL on Nov. 20, 1997, and assigned accession no. NRRL B-21887.

Example 11

Construction of Strain CGA364475 (MONO519) (tac/prnABCD)

P. fluorescens strain CGA364475 (a.k.a. MONO519) was derived from the parent P. fluorescens strain CGA267356 by juxtaposition of the tac promoter element from *E. coli* (Example 3, SEQ ID NO:7) with the prnABCD gene cluster (U.S. Pat. No. 5,639,949) in the chromosome such that expression of the prnABCD genes is from the tac promoter. In strain CGA364475, the prnABCD genes are expressed from the strong, constitutive tac promoter rather than the weaker, regulated native prn gene promoter. As a result, this strain produces more of the antifungal metabolite pyrrolnitrin (Table 1) and provides greater biocontrol activity (Table 2) than parent strain CGA267356. New strain CGA364475 was deposited with the NRRL on Nov. 20, 1997, and assigned accession no. NRRL B-21888.

Example 12

Construction of Strain CGA366259 (MONO524) (tac/prnABCD, pE11)

Strain CGA366259 (a.k.a. MONO524) was created by introducing plasmid pE11 (Example 1) containing the native gacA gene derived from *P. fluorescens* strain CGA267356 into *P. fluorescens* strain CGA364475 (Example 11) by conjugation. New strain CGA366259 has been shown to produce higher amounts of the antifungal metabolite pyrrolnitrin (Table 1) and to provide greater biocontrol activity (Table 2) than parent strain CGA267356. New strain CGA366259 was deposited with the NRRL on Nov. 20, 1997, and assigned accession no. NRRL B-21889.

Example 13

Construction of Strain CGA376150 (MONO575) (CGA267355, pE11)

Strain CGA376150 (a.k.a. MONO575) was constructed by introducing plasmid pE11 (Example 1) into the wild-type *P. fluorescens* strain CGA267355 by conjugation. Strain CGA267355 was isolated from soil in Texas. It normally does not produce the antifungal metabolites pyrrolnitrin and 2-hexyl-5-propyl-resorcinol, or the hydrolytic enzyme chitinase. However, upon the introduction of plasmid pE11 containing the gacA gene, strain CGA376150 was demonstrated to produce pyrrolnitrin (Table 1), 2-hexyl-5-propyl-resorcinol, and chitinase and was shown to be an effective biocontrol agent (Table 2). New strain CGA376150 was deposited with the NRRL on Nov. 20, 1997, and assigned accession no. NRRL B-21890.

Example 14

Construction of Strain NOA402208 (MONO630) (gac*3, pPrn)

Strain NOA402208 (a.k.a. MONO630) was constructed by introducing the plasmid pPrn containing the prnABCD gene cluster under the control of the tac promoter (Example 3) into *P. fluorescens* strain CGA375260 (Example 6) by conjugation. Strain CGA375260 differs from the parent strain CGA267356 by a single base change in the gacA coding sequence (SEQ ID NO:9) that renders GacA (SEQ ID NO:10), the protein product of the modified gacA gene and an activator of transcription, active irrespective of phosphorylation by the LemA protein. As a result, strain NOA402208 produces more pyrrolnitrin (Table 1) and has greater biocontrol activity (Table 2) than parent strain CGA267356. New strain NOA402208 was deposited with the NRRL on Nov. 20, 1997, and assigned accession no. NRRL B-21891.

Example 15

Construction of *Pseudomonas fluorescens* Strain NOA402210 (MONO632) (res⁻, pPrn)

Strain NOA402210 (a.k.a. MONO632) was constructed from *P. fluorescens* strain CGA267356 (U.S. Pat. No. 5,348,742) by deletion of a region of the chromosome that resulted in no production of the antimicrobial metabolite 2-hexyl-5-propyl-resorcinol and introduction of the plasmid pPrn by conjugation.

*P. fluorescens* strain CGA319115 is a transposon mutant of the parent strain CGA267356 that is incapable of the production of 2-hexyl-5-propyl-resorcinol and that provides greater biocontrol activity compared to strain CGA267356. A cosmid clone, BL3610, from a gene library of DNA from strain CGA267356 was found that restores production of 2-hexyl-5-propyl-resorcinol to strain CGA319115. An in vivo marker exchange was performed with cosmid clone BL3610 in strain CGA319115 in order to rescue the transposon and the flanking DNA. The cosmid clone BL3610Tn containing the mutagenized genomic DNA from strain CGA319115 with the transposon was thus isolated. A 6.5 kilobase pair (kb) EcoRI DNA fragment from cosmid BL3610 that corresponded to the region in cosmid BL3610Tn that contained the transposon insertion was cloned into plasmid pBluescript II (Phannacea, Inc.) to create plasmid pBL3632.

The DNA sequence of this fragment and the DNA flanking the transposon in strain CGA319115 were determined and compared to reveal the precise location of the transposon insertion in the 6.5 kb DNA fragment. Two unique BclI restriction sites approximately 200 base pairs apart and flanking the transposon insertion site were identified within this region, and the DNA between these sites was deleted by restriction with BclI and religation. A 4.0 kb XhoI DNA fragment derived from the 6.5 kb EcoRI fragment of pBL3632 and containing the deletion of the 200 base pair BclI fragment was cloned into a plasmid vector to facilitate homologous exchange in strain CGA267356. Homologous exchange between this plasmid and the chromosome of strain CGA267356 resulted in replacement of the wild-type region in the chromosome with the deleted DNA of the plasmid, thereby rendering the strain incapable of producing 2-hexyl-5-propyl-resorcinol. Southern hybridization was performed to confirm that the BclI fragment was absent.

This 2-hexyl-5-propyl-resorcinol non-producing deletion mutant of *P. fluorescens* strain CGA267356 was given the strain name NOA402209. Strain NOA402210 was created by introducing plasmid pPrn containing the prnABCD gene cluster under the control of the tac promoter into strain NOA402209.

Strain NOA402210 produces more pyrrolnitrin (Table 1) than the parent strain CGA267356 and it provides greater biocontrol activity (Table 2) compared to the parent strain. Strain NOA402210 was deposited with the NRRL on Nov. 20, 1997, and assigned accession no. NRRL B-21901.

Example 16

Construction of Strain NOA402212 (MONO634) (gac*3, res⁻, pPrn)

Strain NOA402212 (a.k.a. MONO634) was constructed in a manner identical to that described for strain NOA402210 in Example 15 above, except that the strain used as the starting strain for NOA402212 was *P. fluorescens* strain CGA375260 (Example 6) instead of strain CGA267356.

Strain NOA402212 was created by introducing the deletion of the 200 bp BclI fragment into the chromosome of *P. fluorescens* strain CGA375260 to create strain NOA402211 and by the subsequent introduction of the plasmid pPrn containing the prnABCD gene cluster under the control of the tac promoter. This strain produces more pyrrolnitrin (Table 1) than either the parent strain CGA267356 or strain NOA402208 and it provides greater biocontrol activity (Table 2) compared to the parent strain.

Strain NOA402212 was deposited with the NRRL on Nov. 20, 1997, and assigned accession no. NRRL B-21892.

Example 17

Construction of Strain NOA402214 (MONO636) (ATG-gacA, res⁻, pPrn)

Strain NOA402214 (a.k.a. MONO636) was constructed in a manner identical to that described for strain NOA402210 in Example 15 above, except that the strain used as the starting strain for NOA402214 was *P. fluorescens* strain CGA364473 (Example 2) instead of strain CGA267356.

Strain CGA364473 is identical to strain CGA267356 except for a single base change in the coding sequence of the gacA gene. The gacA gene was noted to have the unusual TTG translation start codon. In order to improve translational efficiency of the gacA-specific mRNA, the first base in the coding sequence of the gacA gene was changed to an adenine (A), thus creating the normal ATG translation start codon (SEQ ID NO:4). Strain CGA364473 was further modified in the same manner as strain NOA402212 to contain the deletion of the 200 base pair BclI fragment, creating strain NOA402213, which does not produce 2-hexyl-5-propyl-resorcinol. Strain NOA402214 was created by introduction of the plasmid pPrn containing the prnABCD genes under the control of the tac promoter by conjugation into strain NOA402213.

Strain NOA402214 produces higher amounts of pyrrolnitrin (Table 1) and provides greater biocontrol activity (Table 2) than parent strain CGA267356. Strain NOA402214 was deposited with the NRRL on Nov. 20, 1997, and assigned accession no. NRRL B-21893.

Example 18

Construction of Strain NOA402216 (MONO638) (lac/ATG-gacA, res⁻, pPrn)

Strain NOA402216 (a.k.a. MONO638) contains a chromosomal gacA gene with an ATG translation start codon as in Example 17 that is expressed from the lac promoter of *E. coli*. It also contains a chromosomal deletion of the 200 base pair BclI fragment that results in a 2-hexyl-5-propyl-resorcinol non-producing phenotype. Finally, it contains the plasmid pPrn described in Example 14, which contains the prnABCD gene cluster under regulation of the tac promoter.

The ATG-gacA gene was fused to the lac promoter and integrated into the chromosome of *P. fluorescens* strain CGA267356 essentially as described in Example 7, except that the lac promoter was used instead of the tac promoter. The resulting strain containing the lac/ATG-gacA gene in its chromosome was converted to a 2-hexyl-5-propyl-resorcinol non-producing phenotype by the same method described for the construction of strain NOA402212 (Example 15) to create strain NOA402215. Finally, strain NOA402216 was constructed by introduction of the plasmid pPrn into strain NOA402215.

Strain NOA402216 produces more pyrrolnitrin (Table 1) and provides greater biocontrol activity (Table 2) than parent strain CGA267356. Strain NOA402216 was deposited with the NRRL on Nov. 20, 1997, and assigned accession no. NRRL B-21894.

Example 19

Construction of Strain NOA409063 (MONO686) (pGac*3/Prn)

Strain NOA409063 (a.k.a. MONO686) was constructed from the parent *P. fluorescens* strain CGA267356 by the introduction of a plasmid containing both the gac*3 and prnABCD genes. Plasmid pGac*3/Prn was constructed by cloning the prnABCD gene cluster under the control of the tac promoter as a 6.9 kb BglII fragment (Example 3) into the unique BglII site of the broad host-range plasmid pVK101 (Knauf, V. and Nester, E. *Plasmid* 8:45–54 (1982)) followed by cloning the gac*3 gene (Example 6) as an XhoI DNA fragment into the unique XhoI site. This plasmid was introduced into the parent *P. fluorescens* strain CGA267356 to create strain NOA409063. This strain produces more pyrrolnitrin (Table 1) and provides greater biocontrol activity (Table 2) than the parent strain CGA267356. Strain NOA409063 was deposited with the NRRL on Nov. 20, 1997, and assigned accession no. NRRL B-21902.

Example 20

Construction of Strain NOA409068 (MONO691) (pKT-Prn)

Strain NOA409068 (a.k.a. MONO691) was constructed in a manner identical to that described for strain CGA375258 in Example 3 above, except that plasmid pKT231 was used in strain NOA409068 to maintain the exogenous DNA instead of the plasmid pRK290 used in strain CGA375258.

Strain NOA409068 was created by introducing plasmid pKT-Prn into parent *P. fluorescens* strain CGA267356 by conjugation. Plasmid pKT-Prn was constructed by cloning the 6.9 kb BglII fragment described in Example 3 containing the prnABCD gene cluster from strain CGA267356 with the tac promoter and rrnB transcription terminator, into the broad host-range plasmid pKT231 (Pühler, Vectors for Gram-negative Bacteria. 1985. Elsevier Scientific Publishers).

Strain NOA409068 produces more pyrrolnitrin (Table 1) and provides greater biocontrol activity (Table 2) than parent strain CGA267356. Strain NOA409068 was deposited with the NRRL on Nov. 20, 1997, and assigned accession no. NRRL B-21895.

Example 21

Construction of Strain NOA413174 (MONO706) (res⁻, pKT-Prn)

Strain NOA413174 (a.k.a. MONO706) was created by introduction of plasmid pKT-Prn (Example 20) by conjugation into the *P. fluorescens* 2-hexyl-5-propyl-resorcinol non-producing strain NOA402209 described in Example 15. Strain NOA413174 produces more pyrrolnitrin (Table 1) and provides greater biocontrol activity (Table 2) compared to parent strain CGA267356. Strain NOA413174 was deposited with the NRRL on Nov. 20, 1997, and assigned accession no. NRRL B-21896.

Example 22

Construction of Strain NOA413175 (MONO707) (gac*3, pKT-Prn)

Strain NOA413175 (a.k.a. MONO707) was created by introduction of plasmid pKT-Prn (Example 20) by conjugation into the *P. fluorescens* strain CGA375260 (Example 6). Strain NOA413175 produces more pyrrolnitrin (Table 1) and provides greater biocontrol activity (Table 2) than parent strain CGA267356. Strain NOA413175 was deposited with the NRRL on Nov. 20, 1997, and assigned accession no. NRRL B-21897.

Example 23

Construction of Strain NOA413176 (MONO708) (gac*3, res⁻, pKT-Prn)

Strain NOA413176 (a.k.a. MONO708) was created by introduction of plasmid pKT-Prn (Example 20) by conjugation into *P. fluorescens* strain NOA402211 (described in Example 16). Strain NOA413176 produces more pyrrolnitrin (Table 1) and provides greater biocontrol activity (Table 2) than parent strain CGA267356. Strain NOA413176 was deposited with the NRRL on Nov. 20, 1997, and assigned accession no. NRRL B-21898.

Example 24

Construction of Strain NOA413177 (MONO709) (ATG-gacA, res⁻, pKT-Prn)

Strain NOA413177 (a.k.a. MONO709) was created by introduction of plasmid pKT-Prn by conjugation into *P. fluorescens* strain NOA402213 (described in Example 17). Strain NOA413177 produces more pyrrolnitrin (Table 1) and provides greater biocontrol activity (Table 2) than parent strain CGA267356. Strain NOA413177 was deposited with the NRRL on Nov. 20, 1997, and assigned accession no. NRRL B-21899.

Example 25

Construction of Strain NOA413178 (MONO710) (lac/ATG-gacA, res⁻, pKT-Prn)

Strain NOA413178 (a.k.a. MONO710) was created by introduction of plasmid pKT-Prn by conjugation into *P. fluorescens* strain NOA402215 (described in Example 18). Strain NOA413178 produces more pyrrolnitrin (Table 1) and provides greater biocontrol activity (Table 2) than parent strain CGA267356. Strain NOA413178 was deposited with the NRRL on Nov. 20, 1997, and assigned accession no. NRRL B-21900.

Example 26

Cultivation of Bacteria and Fungi for Screening Assays a. Cultivation of Bacteria The bacterial strains are stored in 20% glycerol at −80° C. prior to use. One loop from the stored culture is suspended in 5 ml Luria Broth (LB: 10 g Bacto-Tryptone, Difco; 5 g yeast extract, Oxoid; 0.25 g $MgSO_4H_2O$; 8 g NaCl; and 1 L distilled water; pH 7) and shaken at 150 rpm and 25° C. overnight. 100 ml LB is inoculated with 1 ml of the preculture and incubated under the same conditions. 10 ml of the last culture are centrifuged (10 min at 10,000 rpm), and the pellet is resuspended in 200 ml saline (0.8% NaCl) giving a concentration of approximately $10^8$ cfu/ml.

For exact determination, a dilution series ($10^0$ to $10^{-8}$, 20 µl in 180 µl) is prepared in microtiter plate and drops of 10 µl are spotted onto Luria Agar (LB with 1.5% Bacto-Agar, Difco) with an Eppendorf pipette. The cfu are counted after 24 hrs incubation at 28° C.

Antibiotics may be added if required for selection of bacteria: tetracycline ~15 µg/ml; kanamycin ~50 µg/ml.

b. Cultivation of *Rhizoctonia solani*

*Rhizoctonia solani* is grown on Potato Dextrose Agar (PDA, Difco) pH 5.6 in a petri dish. A 300 ml Erlenmeyer flask with 25 g millet and 50 ml distilled water is autoclaved and incubated with one agar plug (5 mm diameter) from a PDA culture of *R. solani*. After incubation at 20° C. in the dark for 3 weeks, the overgrown millet is air-dried and ground in a Culatti mill (1 mm sieve, 6000 rpm).

c. Cultivation of *Pythium aphanidermatum*

*Pythium aphanidermatum* is grown on Malt Agar (Oxoid), pH 5.6 in a petri dish. One agar plug (6 mm diameter) from this culture is transferred to a petri dish with 8 ml oatmeal agar (50 g Oatmeal, 3 ml 1.5% cholestrin in ethanol, and 1 L distilled water) with a slant surface. Two hrs later, 13 ml of sterile distilled water are added, and the plates are incubated for 10 to 14 days in the dark. The mycelium that grows from the agar surface into the water is transferred to a mixer and cut into small pieces. The concentration of oospores is counted in a Thoma chamber and adjusted with distilled water to $2 \times 10^4$/ml.

Example 27

Assays For Biocontrol Activity

Preparation of bacterial cultures: All bacteria cultures are cultured in Luria broth for 2 days at 28° C. Bacterial cells are collected by centrifugation and resuspended in water to $10^9$ or $10^8$ bacterial cells/ml. 10 ml of each suspension is used to drench a pot containing 50 ml soil, resulting in $2 \times 10^8$ (high rate, CGA267356 only) or $2 \times 10^7$ cells/ml soil (all strains). Preparation of fungal inocula: *Rhizoctonia solani* is grown on twice-autoclaved millet seed until fully colonized, then air dried for several days. Dried inoculum is ground to a fine powder for use in all assays except the poinsettia assays, in which whole colonized millet seeds are used. A large supply of inoculum is stored at room temperature and used for several months. *Pythium aphanidennatum* is inoculated on twice-autoclaved millet seed and grown for one week. The colonized millet seed is air dried for 2 hours, then used immediately. Pythium-infested millet seed is prepared weekly.

a. Pathosystem *Rhizoctonia solani*—cucumber

One cucumber seed is planted per pot containing a standard commercially available peat/bark type potting soil. The bacterial suspension is drenched on each pot and Rhizoctonia inoculum is broadcast over the surface of the soil. Each treatment in an experiment contains 5 sets of 12 plants which are randomized and placed in greenhouse under automatic sprinklers. Each experiment is repeated a minimum of three times. Stand counts are recorded at 1 and 2 weeks after planting and compared to uninfested and untreated healthy controls and infested and untreated diseased controls.

b. Pathosystem *Rhizoctonia solani*—impatiens

A single hole is drilled in the center of each pot and Rhizoctonia inoculum is broadcast over the surface of the soil and into the hole. One commercially purchased impatiens seedling plug is transplanted into the hole of each pot and bacteria suspension is applied as a drench. Each treatment in an experiment contains 5 sets of 12 plants which are randomized and placed in greenhouse under automatic sprinklers. Each experiment is repeated a minimum of three times. Stand counts are recorded at 1 and 2 weeks.

c. Pathosystem *Rhizoctonia solani*—poinsettia

The bacterial suspension is drenched on strips of ten Oasis rooting cubes (the cell suspensions were adjusted so that each 50 ml cube was drenched with 40 ml of suspension), resulting in $2 \times 10^8$ or $2 \times 10^7$ cells/ml of cube, and one commercially purchased poinsettia cutting is inserted into each cube in the normal method for rooting. Five Rhizoctonia-infested millet seeds are placed in the middle of the strip (between plants 5 and 6), and the strips are placed in the greenhouse under automatic sprinklers. Each treatment in an experiment contains 4 rooting strips with 10 cuttings each and each experiment is repeated a minimum of three times. Stand counts are recorded at 10 days and 21 days after planting.

d. Pathosystem *Pythium aphanidermatum*—cucumber

One cucumber seed is planted per pot and the bacterial suspension is drenched on top of each pot. Pythium inoculum is broadcast over the surface of the soil and replicates are randomized and placed in the greenhouse under automatic sprinklers. Each treatment in an experiment contains 5 sets of 12 plants and each experiment is repeated a minimum of three times. Stand counts are recorded at 1 and 2 weeks.

Example 28

Extraction of Antifungal Metabolites

Active antifungal metabolites such as pyrrolnitrin (prn) can be extracted from the growth medium of bacterial strains that produce inhibitory antibiotics. For example, using strain CGA376146, this can be accomplished by extraction of the growth medium with 80% acetone followed by removal of the acetone by evaporation and a second extraction with diethyl ether. The diethyl ether is removed by evaporation and the dried extract is resuspended in a small volume of methanol. Alternately, the antifungal metabolites can be extracted with methanol using conventional methods. Small aliquots of the antibiotic extract applied to small sterile filter paper discs placed on an agar plate will inhibit the growth of *Rhizoctonia solani*, indicating the presence of the active antibiotic compound.

Example 29

Combination of Biocontrol Strain With Fungicides

The biocontrol strains of the invention are each applied to non-sterile soil as a drench at $2 \times 10^8$ cfu/ml soil, while metalaxyl fungicide is either drenched (Ridomil at 0.02, 0.5, or 2 ppm) or coated onto seeds (Apron at 35 g a.i./100 kg seed). *Pythium aphanidermatum* is introduced as an oospore suspension (1400 spores/ml soil). *Rhizoctonia solani* is introduced as a pelleted millet powder (5 mg in the center of each pot). After incubation for 19 days in the greenhouse, the hypocotyls of cotton seedlings are rated for disease on an observation scale.

Almost complete control of damping-off may be achieved when one of the biocontrol strains is applied together with Ridomil at 2 ppm. Using Apron instead of Ridomil results in the same level of control. Each of the biocontrol strains alone still gives significant suppression of both pathogens. Metalaxyl fungicide alone, however, fails to control the disease complex. 0.2 ppm Ridomil alone gives approximately 40% suppression of *Pythium aphanidennatum*. However, the combination of 0.02 ppm Ridomil with one of the biocontrol strains significantly increases the level of control. Thus, the combined application of the biocontrol bacterial strains of the invention with a reduced rate of metalaxyl fungicide achieves almost complete control of the seedling disease complex in cotton caused by *Rhizoctonia solani* and *Pythium aphanidennatum*.

Example 30

Antifungal Compositions

Formulations of antifungal compositions containing as the active ingredient the antifungal metabolites that are produced by the biocontrol strains of the invention and that are inhibitory to the growth of Rhizoctonia and Pythium are produced according to Examples 10 and 11 in U.S. Pat. No. 5,348,742. These formulations include emulsifiable concentrates, solutions, granulates, dusts, wettable powders, extruder granulates, coated granulates, and suspension concentrates.

The antifungal compositions may be used to control or inhibit the growth of a plant pathogenic fungus by applying an effective amount of the biocontrol composition to an environment in which the fungus may grow, to a plant or plant part, and/or to seed.

Example 31

Field Trial of Biocontrol Strains

Cultures of the biocontrol strains are stored in 20% glycerol at −80° C. One loop from the stored culture is suspended in 5 ml Luria Broth (LB: 10 g Bacto-Typtone, Difco; 5 g yeast extract, Oxold; 0.25 g $MgSO_4H_2O$; 8 g NaCl; and 1 L distilled water; pH 7) and shaken at 150 rpm and 25° C. for 24 hrs. 100 ml LB is inoculated with 1 ml of the preculture and incubated under the same conditions. After 16 hrs, the culture is centrifuged for 10 minutes at 10,000 rpm, and the pellet is resuspended in saline (0.8% NaCl) and adjusted to $3 \times 10^9$ cfu/ml (OD2). Thus, 100 ml of culture will give approximately 200–300 ml drench of OD2.

A hemocytomerter and/or spectrophotometer is used to adjust the concentration of bacteria in the drench. Otherwise, a standard salt solution of a known OD (e.g., Phillips' Milk of Magnesia TM=$Mg(OH)_2$) can be used to adjust the OD of the drench. If a centrifuge is not available, the whole culture broth has to be applied; a hemocytometer is then used to determine the cfu/ml.

For exact determination, a dilution series ($10^0$ to $10^{-8}$; 20 μin 180 μl) is prepared in a microtiter plate and drops of 10 μl are spotted onto Luria Agar (LB with 1.5% Bacto-Agar, Difco) with an Eppendorf pipette. The cfu are counted after 24 hrs incubation at 28° C.

250 mL of the bacterial suspension per 10' (=1 rep) are drenched onto the covered seeds (200 seeds per rep). A handheld sprayer or watering can free of pesticide residues is used to apply the drench in a narrow band of approximately 1.5 inches width.

Rhizoctonia and Pythium are prepared for inoculation as in Examples 10 and 11 above.

Emergence is recorded at 10 days after planting to assess pre-emergence damping off. Stands are recorded at 21 days and 28 days after planting to assess post-emergence damping-off.

While the present invention has been described with reference to specific embodiments thereof, it will be appreciated that numerous variations, modifications, and embodiments are possible, and accordingly, all such variations, modifications and embodiments are to be regarded as being within the scope of the present invention. Furthermore, all publications and patent applications mentioned in this specification are indicative of the level of skill of those skilled in the art to which this invention pertains. All publications and patent applications are therefore hereby incorporated by reference to the same extent as if each individual publication or patent application was specifically and individually indicated to be incorporated by reference.

TABLE 1

Pyrrolnitrin production by *P. fluorescens* strain CGA267356 and genetically modified strains derived from it. Pyrrolnitrin was isolated from 3 day old cultures of the strains grown in CMMMAD medium by extraction with methanol and quantified by HPLC analysis.

| Strain | Pyrrolnitrin (mg/liter) |
|---|---|
| CGA267356 (MOCG134) | 40.0 |
| CGA376146 (MONO571) | 40.0 |
| CGA364473 (MONO517) | 45.0 |
| CGA375258 (MONO568) | 175.0 |
| CGA376148 (MONO573) | 150.0 |
| CGA364476 (MONO520) | 50.0 |
| CGA375260 (MONO570) | 65.0 |
| CGA375259 (MONO569) | 160.0 |
| CGA378584 (MONO591) | 70.0 |
| CGA364474 (MONO518) | 38.0 |
| CGA364475 (MONO519) | 50.0 |
| CGA366259 (MONO524) | 72.0 |
| CGA376150 (MONO575) | 75.0 |
| NOA402208 (MONO630) | 250.0 |
| NOA402210 (MONO632) | 120.0 |
| NOA402212 (MONO634) | 320.0 |
| NOA402214 (MONO636) | 330.0 |
| NOA402216 (MONO638) | 360.0 |
| NOA409063 (MONO686) | 245.0 |
| NOA409068 (MONO691) | 109.0 |
| NOA413174 (MONO706) | 63.0 |
| NOA413175 (MONO707) | 79.0 |
| NOA413176 (MONO708) | 55.0 |
| NOA413177 (MONO709) | 160.0 |
| NOA413178 (MONO710) | 128.0 |

TABLE 2

Biocontrol activity of *P. fluorescens* strain CGA267356 and genetically modified strains derived from it. The data presented is the control of Rhizoctonia on three plant types and Pythium on cucumbers only. All data is presented relative to the parent strain, CGA267356, applied at high (H) ( = 100% biocontrol activity) and low (L) ( = 0% biocontrol activity) rates equal to $2 \times 10^8$ and $2 \times 10^7$ cells/g soil, respectively. All other strains were applied only at the low rate so that any relative biocontrol activity greater than 0 represents an improvement compared to the parent strain. All data are the mean of three experiments. nd = not determined.

| | Relative Biocontrol Activity | | | |
|---|---|---|---|---|
| | Rhizoctonia | | | Pythium |
| Strain | Cucumber | Impatiens | Poinsettia | Cucumber |
| CGA267356 (H) | 100 | 100 | 100 | 100 |
| CGA267356 (L) | 0 | 0 | 0 | 0 |
| CGA376146 | 34 | 67 | 29 | 33 |
| CGA364473 | 13 | 88 | 43 | 57 |
| CGA375258 | 87 | 67 | 61 | 32 |
| CGA376148 | 28 | 68 | 133 | 4 |
| CGA364476 | 60 | 0 | 75 | 133 |
| CGA375260 | 102 | 0 | 47 | 83 |
| CGA375259 | 60 | 33 | 52 | 51 |
| CGA378584 | 115 | 45 | 54 | 0 |
| CGA267pPhz | 53 | 10 | 0 | 50 |
| CGA364474 | 32 | 25 | 0 | 18 |
| CGA364475 | 42 | 41 | 5 | 9 |
| CGA366259 | 66 | 38 | 30 | 12 |
| CGA376150 | 33 | 35 | 51 | 83 |
| NOA402208 | 225 | 130 | nd | 0 |
| NOA402210 | 163 | 80 | nd | 0 |
| NOA402212 | 125 | 80 | nd | 0 |
| NOA402214 | 25 | 133 | nd | 0 |
| NOA402216 | 163 | 110 | nd | 0 |
| NOA409063 | 400 | 117 | 102 | nd |
| NOA409068 | 267 | 217 | nd | nd |
| NOA413174 | 100 | 67 | nd | nd |
| NOA413175 | 125 | 17 | nd | nd |
| NOA413176 | 0 | 133 | nd | nd |
| NOA413177 | 167 | 166 | nd | nd |
| NOA413178 | 267 | 0 | nd | nd |

TABLE 3

Genotypes of the different Pseudomonas strains.

| Strain | Genotype |
|---|---|
| CGA267356 (MOCG134) | wild-type strain |
| CGA376146 (MONO571) | CGA321730, pE11[a] |
| CGA364473 (MONO517) | ATG-gacA |
| CGA375258 (MONO568) | pPrn[b] |
| CGA376148 (MONO573) | CGA321730, pPrn |
| CGA364476 (MONO520) | pLem/Gac |
| CGA375260 (MONO570) | gac*3 |
| CGA375259 (MONO569) | tac/gacA, pPrn |
| CGA378584 (MONO591) | cPrn, pLem/Gac |
| CGA267pPhz (MONO597) | pPhz |
| CGA364474 (MONO518) | lac/gacA |
| CGA364475 (MONO519) | tac/prnABCD |
| CGA366259 (MONO524) | tac/prnABCD, pE11 |
| CGA376150 (MONO575) | CGA267355, pE11 |
| NOA402208 (MONO630) | gac*3, pPrn |
| NOA402210 (MONO632) | res$^{-c}$, pPrn |
| NOA402212 (MONO634) | gac*3, res$^-$, pPrn |
| NOA402214 (MONO636) | ATG-gacA, res$^-$, pPrn |
| NOA402216 (MONO638) | lac/ATG-gacA, res$^-$, pPrn |
| NOA409063 (MONO686) | pGac*3/Prn |
| NOA409068 (MONO691) | pKT-Prn[d] |
| NOA413174 (MONO706) | res$^-$, pKT-Prn |
| NOA413175 (MONO707) | gac*3, pKT-Prn |
| NOA413176 (MONO708) | gac*3, res$^-$, pKT-Prn |
| NOA413177 (MONO709) | ATG-gacA, res$^-$, pKT-Prn |
| NOA413178 (MONO710) | lac/ATG-gacA, res$^-$, pKT-Prn |

[a]Plasmid pRK290 carrying an 11 kb EcoRI fragment with the native gacA gene.
[b]Plasmid pRK290 carrying the prnABCD gene cluster under control of the tac promoter.
[c]2-bexyl-5-propyl-resorcinol non-producing phenotype from a chromosomal deletion.
[d]Plasmid pKT231 carrying the prnABCD gene cluster under control of the tac promoter.

TABLE 4

The following strains were deposited with the Agricultural Research Service, Patent Culture Collection (NRRL), 1815 North University Street, Peoria, Illinois 61604, under the Budapest Treaty on the International Recognition of the Deposit of Microorganisms for the Purposes of Patent Procedure. All restrictions on the availability of the deposited strains will be irrevocably removed upon the granting of a patent.

| Strain | Accession Number | Deposit Date |
| --- | --- | --- |
| CGA376146 | NRRL B-21811 | September 5, 1997 |
| CGA364473 | NRRL B-21812 | September 5, 1997 |
| CGA375258 | NRRL B-21813 | September 5, 1997 |
| CGA376148 | NRRL B-21814 | September 5, 1997 |
| CGA364476 | NRRL B-21815 | September 5, 1997 |
| CGA375260 | NRRL B-21816 | September 5, 1997 |
| CGA375259 | NRRL B-21817 | September 5, 1997 |
| CGA378584 | NRRL B-21818 | September 5, 1997 |
| CGA267pPhz | NRRL B-21819 | September 5, 1997 |
| CGA364474 | NRRL B-21887 | November 20, 1997 |
| CGA364475 | NRRL B-21888 | November 20, 1997 |
| CGA366259 | NRRL B-21889 | November 20, 1997 |
| CGA376150 | NRRL B-21890 | November 20, 1997 |

TABLE 4-continued

The following strains were deposited with the Agricultural Research Service, Patent Culture Collection (NRRL), 1815 North University Street, Peoria, Illinois 61604, under the Budapest Treaty on the International Recognition of the Deposit of Microorganisms for the Purposes of Patent Procedure. All restrictions on the availability of the deposited strains will be irrevocably removed upon the granting of a patent.

| Strain | Accession Number | Deposit Date |
| --- | --- | --- |
| NOA402208 | NRRL B-21891 | November 20, 1997 |
| NOA402210 | NRRL B-21901 | November 20, 1997 |
| NOA402212 | NRRL B-21892 | November 20, 1997 |
| NOA402214 | NRRL B-21893 | November 20, 1997 |
| NOA402216 | NRRL B-21894 | November 20, 1997 |
| NOA409063 | NRRL B-21902 | November 20, 1997 |
| NOA409068 | NRRL B-21895 | November 20, 1997 |
| NOA413174 | NRRL B-21896 | November 20, 1997 |
| NOA413175 | NRRL B-21897 | November 20, 1997 |
| NOA413176 | NRRL B-21898 | November 20, 1997 |
| NOA413177 | NRRL B-21899 | November 20, 1997 |
| NOA413178 | NRRL B-21900 | November 20, 1997 |

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
      (A) LENGTH: 10763 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (vi) ORIGINAL SOURCE:
      (A) ORGANISM: Pseudomonas fluorescens
      (B) STRAIN: CGA267356 (aka MOCG134 and aka BL915)

(vii) IMMEDIATE SOURCE:
      (B) CLONE: Plasmid pE11

(ix) FEATURE:
      (A) NAME/KEY: misc_feature
      (B) LOCATION: 210..1688
      (D) OTHER INFORMATION: /product= "methyltransferase"
          /note= "Coding sequence for methyltransferase has
             homology to the cheR and frzF genes from E. coli and
             Myxococcus xanthus, respectively."

(ix) FEATURE:
      (A) NAME/KEY: misc_feature (B) LOCATION: 1906..3633
(D) OTHER INFORMATION: /product= "sensor kinase"
    /note= "Coding sequence for sensor kinase has homology
    to the rcsC, frzE, and bvgS genes of E. coli,
    M. Xanthus, and Borditella pertussis, respectively."

(ix) FEATURE:
    (A) NAME/KEY: misc_RNA
    (B) LOCATION: complement (4616..4691)
    (D) OTHER INFORMATION: /product= "tRNA"
        /note= "(complementary DNA strand) Homology to glyW from
        E. Coli."

(ix) FEATURE:
    (A) NAME/KEY: misc_feature
    (B) LOCATION: complement (4731..5318)
    (D) OTHER INFORMATION: /product=
        "CDP-diacylglycerol-glycerol-3-phosphate-3-phosph
        atidyltrans."
        /note= "Coding sequence for
        CDP-diacylglycerol-glycerol-3-phosphate-3-
        phosphatidyltransfere se has homology to pgsA."

(ix) FEATURE:
    (A) NAME/KEY: misc_feature
    (B) LOCATION: complement (5574..7397)
    (D) OTHER INFORMATION: /product= "UVR exonuclease subunit
        C"
        /note= "Coding sequence for UVR exonuclease subunit C has
        homology to uvrC."

(ix) FEATURE:
    (A) NAME/KEY: misc_feature
    (B) LOCATION: complement (7400..8041)
    (D) OTHER INFORMATION: /function= "response
        regulator/transcription activator"
        /product= "gacA (aka gafA)"
        /note= "Coding sequence for gacA (aka gafA) has homology
        to the uvrY and gacA genes of E. coli and Ps.
        fluorescens, respectively."

(xi) SEQUENCE DESCRIPTION: SEQ ID NO:1:

```
GAATTCGATG ACATGCCGCG CGCCGGCATC GACACGCAAA TGGTCGACCT GGTGCTGCCG      60

GTGGTCGAAA TGCCGCAGAA GCTGCTGGAG CTGTGGCGCA ACTCTCAGCT CATCACCCTG     120

CCGACCGCCA ACGATCCGCA AATCAAGGTC TCGGCGCCGG TGTCCAAACG CGATGCCGCG     180

GCGGCGAACA GCAGCTGCAA GACATCCTGA TGCTGTTGCG CACCGGCACC GGCCATGACT     240

TCAAGCATTA CAAGCGCGCC ACGGTGCTGC GGCGGATCGA GCGCCCGCTG CAGGTCACCG     300

CCCAGCCGGA CCTCGCCGCC TATCACGATT ACCTGCAGAT GCACCCTGAA GAAACCAAGG     360

CGCTGCTGGG CGACATGCTG ATCGGCGTGA CCAATTTCTT TCGCGACCGC GAGGCCTTCG     420

AAGCCCTGGA GCGCAATGTC ATTCCTGCCC TGGTGAAGTC CTTGCAGGAC AGCCAACCGC     480

ACCGTGAAGA CGTGCGCATC TGGTCCGCCG GCTGCTCCAC GGGTGAAGAG GCCTATAGCC     540

TGGCAATCGT CGCCAGCGAG CAGATGGCCC TGGAGGCCTG CAACGCCAAG CTGCAGGTAT     600

TCGCGACCGA TATCGACGAT CGTGCCATCG CCCAGGGACG CAAGGGGGTC TATCCCGAAG     660

CGATCGTTAC CGATGTGCCT CCGCAGCGCA TGCGCCAGTA CTTTTCCCGG GAAAACCAGC     720

ATTACCGGGT GCGCAAGGAG ATTCGCGAAA AGGTGCTGTT CGCCAAGCAC AGCCTGCTGG     780

CGGATCCGCC ATTTTCGCAG ATCGACTTGA TCGTCTGCCG TAACCTGCTG ATCTACCTGG     840

ACCGCGACGT GCAACGGGAG ATCCTGCAGA TGTTCCACTT CGCCCTGCGT CCTGGAGGCT     900

ACCTGTTCCT CGGTTCCTCC GAATCCGCGG ACGGCTGCCA GGATCTGTTC GTGCCGGTCG     960

ACAAGCGCAA CCGCATTTTC CGGGTACGGC CCAACTCGGC CACGGTTCGC CGCGCGCCCA    1020

CCATGCCGCG ACGGCGTACA TGCGCACCAT CGGCAGCCCC CACCCCGTGG AAACCAAGTG    1080

TCTCGCGCAA AACCTCGTTC GCCGACATCC ACCTTCGCGC CCTGGAAAAG TGCGCGCCGC    1140
```

```
CGAGCATGAT CGTCGATGCC AACGCCGACA TCCTGCACAT GAGCGAAGGC GCCGGCCGGT   1200

TCCTGCGCTA TGTCGCGGGG GAAATCACCC GCAACCTGCT GACCCTGATC CAGCCCGAGC   1260

TGCGCCTTGA ACTGCGCACC ACGCTGTTCC AGGTGCAACA GTCCGGTGTT GCGGTGACCG   1320

CCGCCGGGTG CGCATCGAGC GGGAAAAGAA GCCTTGTTTC ATCGACCTCA CAGCCCGCCC   1380

CTTCAAGGAC GAGGAAACCG ACAACGAATA TGTGCTGGTG GTGTTCGAGG AGACCGAGGC   1440

CGACCCACGG GAGCTGCGCG AGACCAGCGC CAGCCAGACG GAAAACCAGA TGCTGGCCAA   1500

CCTCGAGCGG GAGTTGCAGC GGACCAAATT GCACCTGCAG GACACCATCG AGCAATCGGA   1560

AGTCTCCAGC GAGGAGCTCA AGGCGTCGAA CGAAGAAATG CAGGCGCTCA ATGAAGAGCT   1620

GCGCTCGGCC ACCGAAGAGC TGGAAACCAG CAAGGAAGAG TTGCAGTCGA TCAATGAAGA   1680

GCTGCTGACG GTCAATTACG AGCTGAAAAC CAAGGTCGAG GAAACCGACA AGATCAACGA   1740

CTACCTGACC AACCTGATCG CCTCCACCGA CATCGCCACG GTGTTCGTCG ACCGCAACAT   1800

GCGCATCCGC TGGTTCACCC CGCGCGCCAC CGACATTTTC AGCATGCTGC CGGTGGACAC   1860

CGACGCTCAT TACTGGACAT CACCCACCGC CTGAACTACC CGGAAATGGC CGAGGACGCC   1920

GCGACCGTGT TCGAGTCGTT GAGCATGATC GAGCGTGAAG TCAACAGCGA CGATCAGCGC   1980

TGGTACATCG CACGCCTGTT GCCCTATCGC TCCAGCGAAG ACCATATCGA CGGCACCGTG   2040

CTGACCTTCA TCGATATCAC CAAGCGCCGG CTGGCCGAGG AGGAACTGCG CCTGGGCGAA   2100

GAACGCATGC GCCTGGTCGC CGAAAGCACC CATGATTTCG CCATCATCAT CCTCGACAAC   2160

CAGGGCCTCA TCACCGACTG GAACACCGGG GCGCAACTGA TCTTCGGCTA TACCAAGGAC   2220

GAAGTGCTGG GCGCCTATTA CGACCTGATT TTCGCGCCTG AGGACCGCGC CGGCGGCGTG   2280

CCGGAAAGCG AGCTGCTCAC CGCCCGCGAA CACGCCGCA GCGACGATGA ACGCTGGCAT   2340

ATACGCAAGG ACGGCGAGCG CTTTTTCTGC AGCGGCGAAG TCACGCGGCT CAAGGGTGAC   2400

AGCCTGCAAG GCTACGTGAA AATAGCCCGC GACCTGACGG GCCACAAACG CATGCAGGAC   2460

GAGCAGAACC AGAAGCTGAT GGAGACCCAG ACCCACAGCC ACCTCAAGGA TGAGTTTTTC   2520

GCGGTGATGT CCCATGAACT CAAGCATCCG CTCAACCTGA TCCAGCTCAA CGCCGAGTTG   2580

CTGCGTCGCC TGCCGACGAC CAAGGCGGCC GCCCCTGCCC TCAAGGCGGT CAATACCATT   2640

TGCGAGGCTG TCTCCAGCCA GGCGCGGATC ATCGACGACC TGCTGGATGT GCGGCGTTTG   2700

CGCACCGGCA AGCTCAAGCT GAAGAAACAG CCGGTGGATC TTGGCCGGAT CCTGCAGGAC   2760

ATCCATACCG TGGTGCTCAG CGAAGGGCAT CGCTGCCAGG TGACGCTGCA AGTGCCGTTG   2820

CCACCGCAAC CGCCGTTAAT GATCGATGCC GATGCGACGC GGCTGGAGCA GGTGATCTGG   2880

AACCTGGTGA CAACGCCCT GAAATTCACC CCGGCCAATG GCTTGGTCCA GTTGATCGCC   2940

CAGCGGGTCG AGGATAAGGC GCACGTGGAT GTCATCGACA GCGGCGTGGG CCTGGCCGAG   3000

GAAGACCAGA ACAAGGTGTT CGACCTTTTC GGCCAGGCGG CCAACCAGCA CGGCACTCAT   3060

CAACGCGACG GGCTGGGCAT CGGCCTGTCA CTGGTGCGCC AGCTGGTGGA AGCCCACGGC   3120

GGCTCGGTCA GCGTGCAGTC GAAGGGGCTG GGCCAGGGAT GCACCTTTAC CGTGCTCTTG   3180

CCCCTGAGCC ACCCCAACGA CAGCGCTCCC AAACAGCCCG CGTCGCGGGG TGTCGAACGC   3240

CTTGCCGGCA TCAAGGTGCT GCTGGTGGAC GACTCGCGGG AAGTCATGGA AGTCCTGCAA   3300

CTGCTGCTGG AGATGGAGGG CGCGCAAGTC GAGGCCTTCC ACGACCCGCT GCAGGCCTTG   3360

GGCAATGCCA GGAACAACAG TTACGACCTG ATCATTTCAG ACATCGGCAT GCCGATTATG   3420

AACGGCTACG AACTGATGCA GAACCTGCGC CAGATCGCTC ACCTGCACCA TACGCCAGCG   3480

ATTGCGCTGA CCGGTTACGG CGCCAGCAGC GACCAGAAGA AGTCCCAGCA TGCGGGATTC   3540
```

```
GATCGGCATG TGAGCAAACC CGTGGCTCAG GACCCGCTGA TCGACCTGAT CAGGGAGCTG   3600

TGCAGCCAGG GCTTGCGCTC GGCTGAGCAC TGATGGTCTA GACCCGGCGA ACCCACCTCG   3660

TCGGCCTTGA GCGCGGCGAG CGCCATTGCC TGCTGGGCAG CTATTCACGC TTGCGGATCG   3720

TCGCGCCTGC GGGCCACCGC CTCTTTGATG GCTTGCTCAT AGGCGGCGTT GGCCTGGTCC   3780

TTGAGCTTGA GCCAATCGTC CCAATCGATC ACGCCGTTGC GCAGCAACTC CTCGGCCGCG   3840

CTTAACAGCG CCTGATGCCA GGCGTCCGGC GAGCCGGAAC GGTAGTCACG GTCTTCCAGC   3900

AGGCCTTGCC AGGCGTCCAG TTCCGGTGTC TTGCGTTCAT TGACCATGGC AGCCACGGCC   3960

TTTGTTCATT GCCGATAAAT CGGCGAGTGG GTGGTGGGTT TCTCGGATAT GCGCCCTGTC   4020

CTGCTCGAGA ACGGCCAGGC CGGGACATTG CTCAACGGTC AGCGACCGGA TGGAGCTCGA   4080

GCGGCATGCC ATCGACCAGC GTCAAGGTCA GGTTCTCGAT GGTGCCGGCG ATCCGGTCCT   4140

TGAATACCGG TTCGCCGTCC GGATCCAACT CATCGTAGAA AAAGCGCGTG CCTTCGAGCC   4200

AGCCAATGGT CGTTTGCAGG TCCGGCCCCA GGTAATACTT GCCGTCAAGG AAAAACCCGG   4260

TAAAGGGCTC CACCCGCTCG CGATTCTCAA TGACATAACG TATTCCAGCG TGCATACCTG   4320

TCGATTTATC GAGCATGGCG TCGATCTCCC AGCAGATGAA TCCGGTAGAC CGCGTGGCTT   4380

TTTCACTGTT CCTTTTGATT GCCCGCCCGA CGCTGGCGAG CCTTGCTCGC GCGTCCTGGC   4440

CGCATTGCGC GGCGAATGGG CGACGTCGAA TCCGATCTGC AAGTGCCCAG CTAGCGGCCC   4500

GGCCACGGCA ATACGGGCTT CAGGTACGGC TTAGAAAGAA GAATGACGAT TGGCTCGACA   4560

TATTTTTTGG CGCAAAAAAA AATGGACCTC TTTTCAGAGG TCCATTTTTA ATATTTGGAG   4620

CGGGAAACGA GACTCGAACT CGCGACCCCG ACCTTGGCAA GGTCGTGCTC TACCAACTGA   4680

GCTATTCCCG CGTCTTGGTG GTGTGCATTT TATAGAAATT CGAAACTGCG TCAACCCCTT   4740

GATTCAAAAA GTTTTATTTC TTTTCTACCA TCGGTCTTCA GGTGCGGCCA GGCAGCGCGC   4800

AGGTACTGCA ACATCGACCA CAGGGTCAGC CCTCCGGCGA TCAGCAGGAA GGCATAACCC   4860

AGCAGCACCC AGAAGGTGAA GGCCGGCGGA TTGGCCAGCA GGATCACCAG CGCCAGCATC   4920

TGCGCGGCAG TTTTCCGATT TGCCCATGTT GGACACCGGC CACCTGGGCG CGTGCGCCCG   4980

AGCTCGGCCA TCCACTCGCG AAGGGCGGAC ACCACGATTT CACGCCCGAT GATCACCGCT   5040

GCCGGCAGGG TCAGCCACAG GTTGCCGTGC TCTTGCACCA GCAGCACCAG GGCCACCGCC   5100

ACCATCAACT TGTCGGCCAC CGGATCGAGG AAGGCCCCGA ACGGCGTGCT CTGCTCCAGA   5160

CGCCGCGCCA GGTAGCCATC AAGCCAGTCG GTGGCCGCGG CGAACGCAAA GACGGAACTG   5220

GCGGCCATGT AGCTCCAGTT GTAAGGCAGG TAAAACAGCA AAATGAAGAT CGGGATGAGC   5280

AGAACGCGTA GAACGGTGAT CAGATTAGGG ATATTCATCG GCACAACTGG CTACGAGGTG   5340

AGTGGCAATC TACTCGGAAA AGACAGCAGA TGAGGTAGCA CGGCCATTCT ACGGGCTTCT   5400

GCCACAGCGT GTCTAACACT GTTCCAAGAC TTCGGGCCGC TCGAAAGAGC AACTTCAGAA   5460

GGTCTACACG CGCAAAATAA GACATTCAGT TCTTCTGTAA GTACCGTGTA GATCGGGATC   5520

TATCAGCGGT GCCCCGCCAA AAAGGAAGCC TTGAAGCTTC CTTGAGCGCT CCCCTACTCG   5580

CTATGCAAGT TCGCATAAAT CAGCTCAGCG AGCTTTTTAC TGATCCCCGG CGCTTTGGCG   5640

ATCTCCTCAA TGCTGGCGCG AGACAGTTCC TGCAACCCAC CAAAGTGTTT CAACAGGTCG   5700

CGGCGGCGCT TGGGGCCGAC GCCGGCCACG TCTTCGAGGG TCGAAGTGCG GCGGGTCTTT   5760

CCGCGACGGG CGCGGTGGCC AGTGATGGCG AAACGGTGAG CCTCGTCGCG GATCTGCTGG   5820

ATCAGGTGCA GCGCCGGCGA GTCGCCCTTG AGGGTGAACT CATGGGCGGC ATCGTTGAGG   5880

TAGAGGGTCT CGAAACCGGT CTTGCGCGTC GCACCCTTGG CCACACCCAG CAGGATCAGG   5940
```

```
TCAGGCACCG CCAACTCGTT GAGCACGTCG CGGGCCATGG ACAGCTGGCC CTTGCCGCCG    6000

TCCACCAGCA GGATGTCCGG CAACTTGCCC TCGCCGTCCT TGAGTTTGCT GAAGCGTCGT    6060

GTCAGGGCCT GGTGCATCGC CGCATAGTCA TCGCCGGCGG TGACGCCTTC GATGTTGTAG    6120

CGCCGATAGT CGGACTTCAG CGGCCCTTCC GGACCGAACA CCACGCAGGA CGCCACGGTC    6180

GCCTCGCCGC TGGAGTGGCT GATGTCGTAG CACTCCAGGC GTTGCGGTGG CTCGTCCAGG    6240

TTCAGCACTT CGGCCAGGGC CTCGAAACGC GCCGCCACAT GCTGCCGGTT GGCCAGGCGC    6300

GCACTCAGCG CCTGTTCGGC GTTGGTCACT GCCAATTGCT GCCAGCGCGC CCGCGTACCG    6360

CGCACCCGGT GGCTGATGCT CAGCTCGCGG CCACGCAGCT CCTGGATCGC CGCGATCAGG    6420

GCCGGGAAAT CCTCATGGAC CACGTTGACG ATCAGCTCGC TGGGCAGGTC GCGCTCCGGG    6480

CTGCTGAGAA AGTACTGGCC GAGGAAGGCC GACATGACTT CGGCCACCTC TTCCTCGATG    6540

CCCACCTGGG GAAAGAAGTT CTTGCTGCCC AGCACCCGCC CGCCCCGCAC GCTGATCAGG    6600

TGCACACAGG CGCCGCCCGG GTTGACGAAG GCCGCGACCA CGTCGACGTC GCCACTGCCG    6660

CCTTCCATGC TCTGCTGGTC CTGGACCCGT CGCAGCAGGG AAATCTGGTC GCGCAGCTCA    6720

GCGGCCTTTT CGAAGTCCAG GGTGCTGGCC GCCTGCTCCA TGCCGGCCGA CAGTTCGTCG    6780

GTCAGGGCAT TGCTGCGGCC TTCGAGGAAC ATCACCGAGT GGCGCACATC CTCGGCGTAC    6840

ACCTCGGCCT CCACCAGGCC GACGCACGGC GCCTTGCAGC GCTTGATCTG ATATTGCAGA    6900

CATGGCCGGG TGCGGTTCTT GTAGTAGCTG TCCTCGCACT GGCGGACCAT GAAGGTCTTT    6960

TGCAGCAGGC TGAGGCTCTC GCGAATGGCC CCGGCGCTGG GGTACGGGCC GAAATACTTG    7020

CCCTTCTGCT TCTTCGCCCC ACGATGGATG CTGAAACGCG GAAACTCGCC GTCCGAGAGA    7080

AACACATAGG GATAGGACTT ATCGTCGCGC AGCAGGATGT TGTACGGCGG CCGCCATTCC    7140

TTGATCAGCG TCTGCTCGAG CAGCAGGGCT TCGGTCTCGT TGGCGGTGAT GGTGGTTTCG    7200

ATCTGCGCGA TGCGCCCCAC CAGGGCAGCG GTCTTGGGCG CCAGGCCGGT CTTGCGAAAG    7260

TAGCTGGCCA GGCGGCTCTT CAGGTTCTTG GCTTTACCGA CGTACAGCAG ACGCGTATCG    7320

CTGTCGAACA TGCGATACAC GCCAGGACGG CCACTGCAGG TGGAAAGAAA AGCACTGGGA    7380

TCAAACGGGT CGGTCATTGT CAGGCACTGG CATCGACCAT GCCGTGGCGA ACCGCCAGCA    7440

ATGTCAGTTC AACATCGCTG CTGATCGAGA GCTTTTCGAA GATGCGGTAA CGGTAGGTAT    7500

TAACGGTTTT CGGAGACAGG CACAGCTTGT CGGAGATGAT CTGCACTTTC TGGCAGCCGA    7560

CAATCATCAG CGCGATCTGG ATTTCCCGCT CGGACAAAGC ATCGAACGGT GAATCACTGG    7620

AAGGCTGGAA TGACTTGAAC ACCAACTGCT GGGCAATTTG CGGGCTGATG TAACGCTGGC    7680

CGGCAAACAC CAGGCGAATG GCCTGCACCA TTTCATTGAG GCCCGCCCCC TTGGTCAGGT    7740

AACCCGCCGC GCCGGCTTGC AGCAAGCGGG TCGGGAACGG ATCTTCTTCA CACACGGTGA    7800

CGGCCACGAC TTTGATATCC GGGTGACTGC GCAACAATTT GCGCGTGGCT TCAAGACCGC    7860

CGATCCCGGG CATCTTGACG TCCATGAGGA CCACATCGGG TTTCAACTCC CGGGCCTTGA    7920

GCAGGGATTC CTCCCCTGAC TCGGCCTGGC CGACCACTTG CAGGCCATCG ATGTCAGCCA    7980

GCATTCGTGT AATACCTGTA CGAACGAGAT CATGGTCATC GACTACTAGC ACCCTAATCA    8040

AGCAGACACC TCGCGATTTG GGTCTTATAG GTTGCCGGAC ACCTTAGCAA AAAAGCAGCG    8100

TGCTGACCTA ATGACAAACA CCATATAAAA AGCACTTGTT CATCAGGGGT ATCCGGTGGA    8160

TGGTTGATGC GCTGCGAACG CCCTGCCCTA AGGCTCTCGG GCGTCCGCCT TTCTTTTCAT    8220

GAGGCTGGAA ACCGAAAGCT CGGCAAGGGT ATGGGTCAGG TGCCGGATCG CGTCCTGATC    8280

TTCCTTGTAC AAGGCCCGGA TAACTGACGA GGCTTTTCTC TTCGCTCTGG CTGAGATTCT    8340
```

| | |
|---|---:|
| CAGCCCTGGT CGGGGTCCGC CTGCCGGTCA CTATATAAAG GACATCGACC CCTTTTGTCG | 8400 |
| CCACCCGGGA CAAGTAATCC GCCTTGGGCA CACGGTCTCC ACTTTCATAT CTGCCTTGGG | 8460 |
| CATTGGCTTC CACGCCGCCA ACTTCACCAA ATTTTTTCTG CGACAACCCC AGGCGTTCCC | 8520 |
| TTTCCTGTCG TCAACCGCGA ACCGATTCCA CTCATTTGGA TGTATGATCC TTTTTTATGC | 8580 |
| ACCCCTAGGG GTGTTACACC CTTCAAGCAT TGAACAAATT TGAACGGTTT TGAACTATGC | 8640 |
| CCGGTTATCC GCACTGCCGC ACAAGCCAAG GCCTGGCTTG AACATCAAGG TAAATCGGTT | 8700 |
| CAACAGTTCG CTCGTGATCA CGGGGTCGAT CCAGCCACCA CTTATCAGGT ATTGGCTGGC | 8760 |
| CGCAAGAAAG GACGGCGCGG CGAGGCGCAC AAGGTGACCG TATTGCTGGG CATGAAAGAC | 8820 |
| GGCGTCATCC TGGCCGAACC CGAGGGTCCC GACCAGACGC CCGCCTGATC TTCGAATGCC | 8880 |
| ATCATCCTGC CGGGAAGAAT CAACTGGCGG CTACGCCTCC ACGGCGCTGC TTCGCTCCAT | 8940 |
| CCGCAGAAAA CACTCGTCTT CCCCGACCAC TTTCAGCCCC ATCCGCCCAT AAAGCGCCTG | 9000 |
| CGCCGGATTG TCCTTGAACA CCGTCAGCCG CAGCAGCCCA CGCCGCTCGT CATGCGCCAT | 9060 |
| CGCACGCACC TGTTCGATGG TCCAGGCCCC GACGCCTTGC CCGCGCGACG CCTCGAGCAC | 9120 |
| ATGCAATTCA CGAATGTACA AAGCCTTGGC ATCGCGACTC AGGCTGACGA ACCCCAGCAC | 9180 |
| CCTGGCGCCC TGGCAGATCA ACAGGTTCTG CCGACCGGCC CAGGCCACAT CGAAGGCCTC | 9240 |
| ATCCAGCCAC AACAGGTCGT GACGAATGTG ATAACCCAGC ATGGTGCTGC GGGTCAGGTC | 9300 |
| GCGGGCGAAC ACCAGATCCT CGTGGCTGCC GGCCGGACGT AGCTGCAGGC CGTTCAAGGC | 9360 |
| GCGTCAACCG GCAATGACTG GCCACTCCAG CGCCCGGCAT TGCGCCTGGC AATCAGCAGT | 9420 |
| TCGTCGCCTG TACCGGCCGA AGCCATGATC AGCCCGCCGC CGGCGCCCCA GATCGCGCTA | 9480 |
| CGCCCCGCCG ACACCCAGCC CCCGGTCGGC CCGCCGTGGT TGGCCATCAG CACCAGCATT | 9540 |
| GCGTGCTCGG CGGCATACCC CTGCAACAAG GCACTGTCCG CGGCATAGCC TGTTTCGCCG | 9600 |
| ATCAAAACGC CAGCGGCATA GATGCCGGCA CCGGAGTGCG CCGCCGCACG CGCGTGGCTG | 9660 |
| GCCTGGGAGA AGTCGGCGCA CACCGCCAGG GCCACCTGGT CTTCGGCGAA CCTCAGGTTC | 9720 |
| GCGCCACCGG TGCCGGGGCT GAATACCCGC TCCTCGCCAG CATGCAGATG CTGCTTGCTG | 9780 |
| TACACCGCCA GCGAACCATC GGCGGCCAGC ACCAGGGCGC CGATCAACAG CGGCCCCTCG | 9840 |
| ACCGACAGGC GGACGGGCAT GCCCACCACC GCTGTTACGC CCCGCTCCCG GGCCAGGTCG | 9900 |
| CGCAACGGTT GCAACAGCGG GCTCTGCGGC AGTATCGCCA GCTCGGCCGC CAGCGCGGGC | 9960 |
| TCATAACCGG TCAGGGACAG CTCGGGAAAT ACCAGCAATT GCACGCCCTG CTCCGCCGCG | 10020 |
| ACGCGGATAA AGGCCTGGTG CCGGGCGATA TTGCCCGGCA GGTCTCCGGC AACGGAAATC | 10080 |
| GACTGGGCGG CGGCAAGGGT CAGCATGGTC ATGGTTCAAC CTGAATCGGC ATTCGGGAGG | 10140 |
| GCGTGGCGAG TGTGTCATAA AAAACTCAAA GCGCTTCACT CATAGACAGC GACTGAAAAC | 10200 |
| GCAATAGGAT TTTCTGATTG AACCGCGCCC CCGGCCTCTA GTAAGCTCGG CCCACTTCAC | 10260 |
| GGAGAAACAG CATGTCGTCC CTCACCCTTA CCATGCATCG TCACACTGCC AGCGCCGCGC | 10320 |
| GCTCCGGTGC GGCTGCCTGG GTGAAAAACG CCTGCGCTCC GGCGGGCTTT TATTTTGGGT | 10380 |
| ATTGGTTTAG CCACTGGCGC GCCTGATACC CAAACGGCGC CCACTTGAAC GGGTCGCCTA | 10440 |
| CCAGAGAAAA TCTCACCCCC GGTCGGCCTC CCGACCGGGG GTTTTGTTTT TCTGGGCCGA | 10500 |
| AGATTTTTAA CCGCGACTTC TTAAGCAACA CACCGAACTT ACCGAGGATT GAACCATGAA | 10560 |
| CTACGCCACC TATTACCGTT ACGACACTTG CACCACCTGG CGATTTAGCA GCCTCCGTTC | 10620 |
| GGGACAGCCT GCCGCCTCCG ATCGGTCACC TACTGGTGGC AAACATACCT GCACAGCCAA | 10680 |

```
TCCGGCCAAT TGTCGAACAC CCCAGTAGGG CCGCGCGCGG GAAATCACCC GCCGCCTGCC    10740

CAGGAAGCCT TGAACATGAA TTC                                            10763
```

(2) INFORMATION FOR SEQ ID NO:2:

(i) SEQUENCE CHARACTERISTICS:
        (A) LENGTH: 642 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Pseudomonas fluorescens
        (B) STRAIN: CGA267356 (aka MOCG134 and aka BL915)

(ix) FEATURE:
        (A) NAME/KEY: CDS
        (B) LOCATION: 1..639
        (D) OTHER INFORMATION: /transl_except= (pos: 1 .. 3, aa: Met (xi) SEQUENCE DESCRIPTION: SEQ ID NO:2:

```
TTG ATT AGG GTG CTA GTA GTC GAT GAC CAT GAT CTC GTT CGT ACA GGT       48
Met Ile Arg Val Leu Val Val Asp Asp His Asp Leu Val Arg Thr Gly
 1               5                  10                  15

ATT ACA CGA ATG CTG GCT GAC ATC GAT GGC CTG CAA GTG GTC GGC CAG       96
Ile Thr Arg Met Leu Ala Asp Ile Asp Gly Leu Gln Val Val Gly Gln
             20                  25                  30

GCC GAG TCA GGG GAG GAA TCC CTG CTC AAG GCC CGG GAG TTG AAA CCC      144
Ala Glu Ser Gly Glu Glu Ser Leu Leu Lys Ala Arg Glu Leu Lys Pro
         35                  40                  45

GAT GTG GTC CTC ATG GAC GTC AAG ATG CCC GGG ATC GGC GGT CTT GAA      192
Asp Val Val Leu Met Asp Val Lys Met Pro Gly Ile Gly Gly Leu Glu
     50                  55                  60

GCC ACG CGC AAA TTG TTG CGC AGT CAC CCG GAT ATC AAA GTC GTG GCC      240
Ala Thr Arg Lys Leu Leu Arg Ser His Pro Asp Ile Lys Val Val Ala
 65                  70                  75                  80

GTC ACC GTG TGT GAA GAA GAT CCG TTC CCG ACC CGC TTG CTG CAA GCC      288
Val Thr Val Cys Glu Glu Asp Pro Phe Pro Thr Arg Leu Leu Gln Ala
                 85                  90                  95

GGC GCG GCG GGT TAC CTG ACC AAG GGG GCG GGC CTC AAT GAA ATG GTG      336
Gly Ala Ala Gly Tyr Leu Thr Lys Gly Ala Gly Leu Asn Glu Met Val
            100                 105                 110

CAG GCC ATT CGC CTG GTG TTT GCC GGC CAG CGT TAC ATC AGC CCG CAA      384
Gln Ala Ile Arg Leu Val Phe Ala Gly Gln Arg Tyr Ile Ser Pro Gln
        115                 120                 125

ATT GCC CAG CAG TTG GTG TTC AAG TCA TTC CAG CCT TCC AGT GAT TCA      432
Ile Ala Gln Gln Leu Val Phe Lys Ser Phe Gln Pro Ser Ser Asp Ser
    130                 135                 140

CCG TTC GAT GCT TTG TCC GAG CGG GAA ATC CAG ATC GCG CTG ATG ATT      480
Pro Phe Asp Ala Leu Ser Glu Arg Glu Ile Gln Ile Ala Leu Met Ile
145                 150                 155                 160

GTC GGC TGC CAG AAA GTG CAG ATC ATC TCC GAC AAG CTG TGC CTG TCT      528
Val Gly Cys Gln Lys Val Gln Ile Ile Ser Asp Lys Leu Cys Leu Ser
                165                 170                 175

CCG AAA ACC GTT AAT ACC TAC CGT TAC CGC ATC TTC GAA AAG CTC TCG      576
Pro Lys Thr Val Asn Thr Tyr Arg Tyr Arg Ile Phe Glu Lys Leu Ser
            180                 185                 190
```

```
ATC AGC AGC GAT GTT GAA CTG ACA TTG CTG GCG GTT CGC CAC GGC ATG       624
Ile Ser Ser Asp Val Glu Leu Thr Leu Leu Ala Val Arg His Gly Met
        195                 200                 205

GTC GAT GCC AGT GCC TGA                                               642
Val Asp Ala Ser Ala
    210
```

(2) INFORMATION FOR SEQ ID NO:3:

(i) SEQUENCE CHARACTERISTICS:
        (A) LENGTH: 213 amino acids
        (B) TYPE: amino acid
        (D) TOPOLOGY: linear (ii) MOLECULE TYPE: protein (xi) SEQUENCE DESCRIPTION: SEQ ID NO:3:

```
Met Ile Arg Val Leu Val Val Asp Asp His Asp Leu Val Arg Thr Gly
 1               5                  10                  15

Ile Thr Arg Met Leu Ala Asp Ile Asp Gly Leu Gln Val Val Gly Gln
                20                  25                  30

Ala Glu Ser Gly Glu Glu Ser Leu Leu Lys Ala Arg Glu Leu Lys Pro
            35                  40                  45

Asp Val Val Leu Met Asp Val Lys Met Pro Gly Ile Gly Gly Leu Glu
        50                  55                  60

Ala Thr Arg Lys Leu Leu Arg Ser His Pro Asp Ile Lys Val Val Ala
65                  70                  75                  80

Val Thr Val Cys Glu Glu Asp Pro Phe Pro Thr Arg Leu Leu Gln Ala
                85                  90                  95

Gly Ala Ala Gly Tyr Leu Thr Lys Gly Ala Gly Leu Asn Glu Met Val
            100                 105                 110

Gln Ala Ile Arg Leu Val Phe Ala Gly Gln Arg Tyr Ile Ser Pro Gln
        115                 120                 125

Ile Ala Gln Gln Leu Val Phe Lys Ser Phe Gln Pro Ser Ser Asp Ser
    130                 135                 140

Pro Phe Asp Ala Leu Ser Glu Arg Glu Ile Gln Ile Ala Leu Met Ile
145                 150                 155                 160

Val Gly Cys Gln Lys Val Gln Ile Ile Ser Asp Lys Leu Cys Leu Ser
                165                 170                 175

Pro Lys Thr Val Asn Thr Tyr Arg Tyr Arg Ile Phe Glu Lys Leu Ser
            180                 185                 190

Ile Ser Ser Asp Val Glu Leu Thr Leu Leu Ala Val Arg His Gly Met
        195                 200                 205

Val Asp Ala Ser Ala
    210
```

(2) INFORMATION FOR SEQ ID NO:4:

(i) SEQUENCE CHARACTERISTICS:
        (A) LENGTH: 642 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Pseudomonas fluorescens
        (B) STRAIN: CGA267356 (aka MOCG134 and aka BL915)

(ix) FEATURE:
   (A) NAME/KEY: misc_feature
   (B) LOCATION: 1..3
   (D) OTHER INFORMATION: /note= "TTG initiation codon in native sequence modified to ATG initiation codon."

(ix) FEATURE:
   (A) NAME/KEY: CDS
   (B) LOCATION: 1..639

(xi) SEQUENCE DESCRIPTION: SEQ ID NO:4:

| | | | | | | | | | | | | | | | |
|---|---|---|---|---|---|---|---|---|---|---|---|---|---|---|---|
| ATG | ATT | AGG | GTG | CTA | GTA | GTC | GAT | GAC | CAT | GAT | CTC | GTT | CGT | ACA | GGT | 48 |
| Met | Ile | Arg | Val | Leu | Val | Val | Asp | Asp | His | Asp | Leu | Val | Arg | Thr | Gly |
| 1 | | | | 5 | | | | | 10 | | | | | 15 | |

| ATT | ACA | CGA | ATG | CTG | GCT | GAC | ATC | GAT | GGC | CTG | CAA | GTG | GTC | GGC | CAG | 96 |
| Ile | Thr | Arg | Met | Leu | Ala | Asp | Ile | Asp | Gly | Leu | Gln | Val | Val | Gly | Gln |
| | | | 20 | | | | | 25 | | | | | 30 | | |

| GCC | GAG | TCA | GGG | GAG | GAA | TCC | CTG | CTC | AAG | GCC | CGG | GAG | TTG | AAA | CCC | 144 |
| Ala | Glu | Ser | Gly | Glu | Glu | Ser | Leu | Leu | Lys | Ala | Arg | Glu | Leu | Lys | Pro |
| | | 35 | | | | | 40 | | | | | 45 | | | |

| GAT | GTG | GTC | CTC | ATG | GAC | GTC | AAG | ATG | CCC | GGG | ATC | GGC | GGT | CTT | GAA | 192 |
| Asp | Val | Val | Leu | Met | Asp | Val | Lys | Met | Pro | Gly | Ile | Gly | Gly | Leu | Glu |
| | 50 | | | | | 55 | | | | | 60 | | | | |

| GCC | ACG | CGC | AAA | TTG | TTG | CGC | AGT | CAC | CCG | GAT | ATC | AAA | GTC | GTG | GCC | 240 |
| Ala | Thr | Arg | Lys | Leu | Leu | Arg | Ser | His | Pro | Asp | Ile | Lys | Val | Val | Ala |
| 65 | | | | 70 | | | | | 75 | | | | | 80 | |

| GTC | ACC | GTG | TGT | GAA | GAA | GAT | CCG | TTC | CCG | ACC | CGC | TTG | CTG | CAA | GCC | 288 |
| Val | Thr | Val | Cys | Glu | Glu | Asp | Pro | Phe | Pro | Thr | Arg | Leu | Leu | Gln | Ala |
| | | | 85 | | | | | 90 | | | | | 95 | | |

| GGC | GCG | GCG | GGT | TAC | CTG | ACC | AAG | GGG | GCG | GGC | CTC | AAT | GAA | ATG | GTG | 336 |
| Gly | Ala | Ala | Gly | Tyr | Leu | Thr | Lys | Gly | Ala | Gly | Leu | Asn | Glu | Met | Val |
| | | 100 | | | | | 105 | | | | | 110 | | | |

| CAG | GCC | ATT | CGC | CTG | GTG | TTT | GCC | GGC | CAG | CGT | TAC | ATC | AGC | CCG | CAA | 384 |
| Gln | Ala | Ile | Arg | Leu | Val | Phe | Ala | Gly | Gln | Arg | Tyr | Ile | Ser | Pro | Gln |
| | 115 | | | | | 120 | | | | | 125 | | | | |

| ATT | GCC | CAG | CAG | TTG | GTG | TTC | AAG | TCA | TTC | CAG | CCT | TCC | AGT | GAT | TCA | 432 |
| Ile | Ala | Gln | Gln | Leu | Val | Phe | Lys | Ser | Phe | Gln | Pro | Ser | Ser | Asp | Ser |
| | 130 | | | | | 135 | | | | | 140 | | | | |

| CCG | TTC | GAT | GCT | TTG | TCC | GAG | CGG | GAA | ATC | CAG | ATC | GCG | CTG | ATG | ATT | 480 |
| Pro | Phe | Asp | Ala | Leu | Ser | Glu | Arg | Glu | Ile | Gln | Ile | Ala | Leu | Met | Ile |
| 145 | | | | 150 | | | | | 155 | | | | | 160 | |

| GTC | GGC | TGC | CAG | AAA | GTG | CAG | ATC | ATC | TCC | GAC | AAG | CTG | TGC | CTG | TCT | 528 |
| Val | Gly | Cys | Gln | Lys | Val | Gln | Ile | Ile | Ser | Asp | Lys | Leu | Cys | Leu | Ser |
| | | | 165 | | | | | 170 | | | | | 175 | | |

| CCG | AAA | ACC | GTT | AAT | ACC | TAC | CGT | TAC | CGC | ATC | TTC | GAA | AAG | CTC | TCG | 576 |
| Pro | Lys | Thr | Val | Asn | Thr | Tyr | Arg | Tyr | Arg | Ile | Phe | Glu | Lys | Leu | Ser |
| | | 180 | | | | | 185 | | | | | 190 | | | |

| ATC | AGC | AGC | GAT | GTT | GAA | CTG | ACA | TTG | CTG | GCG | GTT | CGC | CAC | GGC | ATG | 624 |
| Ile | Ser | Ser | Asp | Val | Glu | Leu | Thr | Leu | Leu | Ala | Val | Arg | His | Gly | Met |
| | 195 | | | | | 200 | | | | | 205 | | | | |

| GTC | GAT | GCC | AGT | GCC | TGA | | | | | | | | | | | 642 |
| Val | Asp | Ala | Ser | Ala | | | | | | | | | | | |
| | 210 | | | | | | | | | | | | | | |

(2) INFORMATION FOR SEQ ID NO:5:

(i) SEQUENCE CHARACTERISTICS:
      (A) LENGTH: 213 amino acids
      (B) TYPE: amino acid
      (D) TOPOLOGY: linear (ii) MOLECULE TYPE: protein (xi) SEQUENCE DESCRIPTION: SEQ ID NO:5:

```
Met Ile Arg Val Leu Val Val Asp Asp His Asp Leu Val Arg Thr Gly
  1               5                  10                  15

Ile Thr Arg Met Leu Ala Asp Ile Asp Gly Leu Gln Val Val Gly Gln
             20                  25                  30

Ala Glu Ser Gly Glu Glu Ser Leu Leu Lys Ala Arg Glu Leu Lys Pro
         35                  40                  45

Asp Val Val Leu Met Asp Val Lys Met Pro Gly Ile Gly Gly Leu Glu
     50                  55                  60

Ala Thr Arg Lys Leu Leu Arg Ser His Pro Asp Ile Lys Val Val Ala
 65                  70                  75                  80

Val Thr Val Cys Glu Glu Asp Pro Phe Pro Thr Arg Leu Leu Gln Ala
                 85                  90                  95

Gly Ala Ala Gly Tyr Leu Thr Lys Gly Ala Gly Leu Asn Glu Met Val
                100                 105                 110

Gln Ala Ile Arg Leu Val Phe Ala Gly Gln Arg Tyr Ile Ser Pro Gln
            115                 120                 125

Ile Ala Gln Gln Leu Val Phe Lys Ser Phe Gln Pro Ser Ser Asp Ser
        130                 135                 140

Pro Phe Asp Ala Leu Ser Glu Arg Glu Ile Gln Ile Ala Leu Met Ile
145                 150                 155                 160

Val Gly Cys Gln Lys Val Gln Ile Ile Ser Asp Lys Leu Cys Leu Ser
                165                 170                 175

Pro Lys Thr Val Asn Thr Tyr Arg Tyr Arg Ile Phe Glu Lys Leu Ser
            180                 185                 190

Ile Ser Ser Asp Val Glu Leu Thr Leu Leu Ala Val Arg His Gly Met
        195                 200                 205

Val Asp Ala Ser Ala
    210

(2) INFORMATION FOR SEQ ID NO:6:

(i) SEQUENCE CHARACTERISTICS:
        (A) LENGTH: 7001 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Pseudomonas fluorescens
        (B) STRAIN: CGA267356 (aka MOCG134 and aka BL915)

(vii) IMMEDIATE SOURCE:
        (B) CLONE: pCIB169

(ix) FEATURE:
        (A) NAME/KEY: misc_feature
        (B) LOCATION: 423..2036
        (D) OTHER INFORMATION: /product= "PrnA"
            /note= "ORF1"

(ix) FEATURE:
        (A) NAME/KEY: misc_feature
        (B) LOCATION: 2039..3121
        (D) OTHER INFORMATION: /product= "PrnB"
            /note= "ORF2"

(ix) FEATURE:
        (A) NAME/KEY: misc_feature
        (B) LOCATION: 3167..4867
```

(D) OTHER INFORMATION: /product= "PrnC"
    /note= "ORF3"

(ix) FEATURE:
    (A) NAME/KEY: misc_feature
    (B) LOCATION: 4895..5983
    (D) OTHER INFORMATION: /product= "PrnD"
        /note= "ORF4"

(xi) SEQUENCE DESCRIPTION: SEQ ID NO:6:

```
GAATTCCGAC AACGCCGAAG AAGCGCGGAA CCGCTGAAAG AGGAGCAGGA ACTGGAGCAA      60

ACGCTGTCCC AGGTGATCGA CAGCCTGCCA CTGCGCATCG AGGGCCGATG AACAGCATTG     120

GCAAAAGCTG GCGGTGCGCA GTGCGCGAGT GATCCGATCA TTTTTGATCG GCTCGCCTCT     180

TCAAAATCGG CGGTGGATGA AGTCGACGGC GGACTGATCA GGCGCAAAAG AACATGCGCC     240

AAAACCTTCT TTTATAGCGA ATACCTTTGC ACTTCAGAAT GTTAATTCGG AAACGGAATT     300

TGCATCGCTT TTCCGGCAGT CTAGAGTCTC TAACAGCACA TTGATGTGCC TCTTGCATGG     360

ATGCACGAAG ACTGGCGGCC TCCCCTCGTC ACAGGCGGCC CGCCTTTGAA CAAGGAGTG     420

TTATGAACAA GCCGATCAAG AATATCGTCA TCGTGGGCGG CGGTACTGCG GGCTGGATGG     480

CCGCCTCGTA CCTCGTCCGG GCCCTCCAAC AGCAGGCGAA CATTACGCTC ATCGAATCTG     540

CGGCGATCCC TCGGATCGGC GTGGGCGAAG CGACCATCCC AAGTTTGCAG AAGGTGTTCT     600

TCGATTTCCT CGGGATACCG GAGCGGGAAT GGATGCCCCA AGTGAACGGC GCGTTCAAGG     660

CCGCGATCAA GTTCGTGAAT GGAGAAAGT CTCCCGACCC CTCGCGCGAC GATCACTTCT     720

ACCATTTGTT CGGCAACGTG CCGAACTGCG ACGGCGTGCC GCTTACCCAC TACTGGCTGC     780

GCAAGCGCGA ACAGGGCTTC CAGCAGCCGA TGGAGTACGC GTGCTACCCG CAGCCCGGGG     840

CACTCGACGG CAAGCTGGCA CCGTGCCTGT CCGACGGCAC CCGCCAGATG TCCCACGCGT     900

GGCACTTCGA CGCGCACCTG GTGGCCGACT TCTTGAAGCG CTGGGCCGTC GAGCGCGGGG     960

TGAACCGCGT GGTCGATGAG GTGGTGGACG TTCGCCTGAA CAACCGCGGC TACATCTCCA    1020

ACCTGCTCAC CAAGGAGGGG CGGACGCTGG AGGCGGACCT GTTCATCGAC TGCTCCGGCA    1080

TGCGGGGGCT CCTGATCAAT CAGGCGCTGA AGGAACCCTT CATCGACATG TCCGACTACC    1140

TGCTGTGCGA CAGCGCGGTC GCCAGCGCCG TGCCCAACGA CGACGCGCGC GATGGGGTCG    1200

AGCCGTACAC CTCCTCGATC GCCATGAACT CGGGATGGAC CTGGAAGATT CCGATGCTGG    1260

GCCGGTTCGG CAGCGGCTAC GTCTTCTCGA GCCATTTCAC CTCGCGCGAC CAGGCCACCG    1320

CCGACTTCCT CAAACTCTGG GGCCTCTCGG ACAATCAGCC GCTCAACCAG ATCAAGTTCC    1380

GGGTCGGGCG CAACAAGCGG GCGTGGGTCA ACAACTGCGT CTCGATCGGG CTGTCGTCGT    1440

GCTTTCTGGA GCCCCTGGAA TCGACGGGGA TCTACTTCAT CTACGCGGCG CTTTACCAGC    1500

TCGTGAAGCA CTTCCCCGAC ACCTCGTTCG ACCCGCGGCT GAGCGACGCT TTCAACGCCG    1560

AGATCGTCCA CATGTTCGAC GACTGCCGGG ATTTCGTCCA AGCGCACTAT TTCACCACGT    1620

CGCGCGATGA CACGCCGTTC TGGCTCGCGA ACCGGCACGA CCTGCGGCTC TCGGACGCCA    1680

TCAAAGAGAA GGTTCAGCGC TACAAGGCGG GCTGCCGCT GACCACCACG TCGTTCGACG    1740

ATTCCACGTA CTACAGAGACC TTCGACTACG AATTCAAGAA TTTCTGGTTG AACGGCAACT    1800

ACTACTGCAT CTTTGCCGGC TTGGGCATGC TGCCCGACCG GTCGCTGCCG CTGTTGCAGC    1860

ACCGACCGGA GTCGATCGAG AAAGCCGAGG CGATGTTCGC CAGCATCCGG CGCGAGGCCG    1920

AGCGTCTGCG CACCAGCCTG CCGACAAACT ACGACTACCT GCGGTCGCTG CGTGACGGCG    1980

ACGCGGGGCT GTCGCGCGGC CAGCGTGGGC CGAAGCTCGC AGCGCAGGAA AGCCTGTAGT    2040

GGAACGCACC TTGGACCGGG TAGGCGTATT CGCGGCCACC CACGCTGCCG TGGCGGCCTG    2100
```

```
CGATCCGCTG CAGGCGCGCG CGCTCGTTCT GCAACTGCCG GGCCTGAACC GTAACAAGGA    2160

CGTGCCCGGT ATCGTCGGCC TGCTGCGCGA GTTCCTTCCG GTGCGCGGCC TGCCCTGCGG    2220

CTGGGGTTTC GTCGAAGCCG CCGCCGCGAT GCGGGACATC GGGTTCTTCC TGGGGTCGCT    2280

CAAGCGCCAC GGACATGAGC CCGCGGAGGT GGTGCCCGGG CTTGAGCCGG TGCTGCTCGA    2340

CCTGGCACGC GCGACCAACC TGCCGCCGCG CGAGACGCTC CTGCATGTGA CGGTCTGGAA    2400

CCCCACGGCG GCCGACGCGC AGCGCAGCTA CACCGGGCTG CCCGACGAAG CGCACCTGCT    2460

CGAGAGCGTG CGCATCTCGA TGGCGGCCCT CGAGGCGGCC ATCGCGTTGA CCGTCGAGCT    2520

GTTCGATGTG TCCCTGCGGT CGCCCGAGTT CGCGCAAAGG TGCGACGAGC TGGAAGCCTA    2580

TCTGCAGAAA ATGGTCGAAT CGATCGTCTA CGCGTACCGC TTCATCTCGC CGCAGGTCTT    2640

CTACGATGAG CTGCGCCCCT TCTACGAACC GATTCGAGTC GGGGGCCAGA GCTACCTCGG    2700

CCCCGGTGCC GTAGAGATGC CCCTCTTCGT GCTGGAGCAC GTCCTCTGGG CTCGCAATC    2760

GGACGACCAA ACTTATCGAG AATTCAAAGA GACGTACCTG CCCTATGTGC TTCCCGCGTA    2820

CAGGGCGGTC TACGCTCGGT TCTCCGGGGA GCCGGCGCTC ATCGACCGCG CGCTCGACGA    2880

GGCGCGAGCG GTCGGTACGC GGGACGAGCA CGTCCGGGCT GGGCTGACAG CCCTCGAGCG    2940

GGTCTTCAAG GTCCTGCTGC GCTTCCGGGC GCCTCACCTC AAATTGGCGG AGCGGGCGTA    3000

CGAAGTCGGG CAAAGCGGCC CCGAAATCGG CAGCGGGGGG TACGCGCCCA GCATGCTCGG    3060

TGAGCTGCTC ACGCTGACGT ATGCCGCGCG GTCCCGCGTC CGCGCCGCGC TCGACGAATC    3120

CTGATGCGCG CGACCCAGTG TTATCTCACA AGGAGAGTTT GCCCCCATGA CTCAGAAGAG    3180

CCCCGCGAAC GAACACGATA GCAATCACTT CGACGTAATC ATCCTCGGCT CGGGCATGTC    3240

CGGCACCCAG ATGGGGGCCA TCTTGGCCAA ACAACAGTTT CGCGTGCTGA TCATCGAGGA    3300

GTCGTCGCAC CCGCGGTTCA CGATCGGCGA ATCGTCGATC CCCGAGACGT CTCTTATGAA    3360

CCGCATCATC GCTGATCGCT ACGGCATTCC GGAGCTCGAC CACATCACGT CGTTTTATTC    3420

GACGCAACGT TACGTCGCGT CGAGCACGGG CATTAAGCGC AACTTCGGCT TCGTGTTCCA    3480

CAAGCCCGGC CAGGAGCACG ACCCGAAGGA GTTCACCCAG TGCGTCATTC CCGAGCTGCC    3540

GTGGGGGCCG GAGAGCCATT ATTACCGGCA AGACGTCGAC GCCTACTTGT TGCAAGCCGC    3600

CATTAAATAC GGCTGCAAGG TCCACCAGAA AACTACCGTG ACCGAATACC ACGCCGATAA    3660

AGACGGCGTC GCGGTGACCA CCGCCCAGGG CGAACGGTTC ACCGGCCGGT ACATGATCGA    3720

CTGCGGAGGA CCTCGCGCGC CGCTCGCGAC CAAGTTCAAG CTCCGCGAAG AACCGTGTCG    3780

CTTCAAGACG CACTCGCGCA GCCTCTACAC GCACATGCTC GGGGTCAAGC CGTTCGACGA    3840

CATCTTCAAG GTCAAGGGGC AGCGCTGGCG CTGGACGAG GGGACCTTGC ACCACATGTT    3900

CGAGGGCGGC TGGCTCTGGG TGATTCCGTT CAACAACCAC CCGCGGTCGA CCAACAACCT    3960

GGTGAGCGTC GGCCTGCAGC TCGACCCGCG TGTCTACCCG AAAACCGACA TCTCCGCACA    4020

GCAGGAATTC GATGAGTTCC TCGCGCGGTT CCCGAGCATC GGGGCTCAGT TCCGGGACGC    4080

CGTGCCGGTG CGCGACTGGG TCAAGACCGA CCGCCTGCAA TTCTCGTCGA ACGCCTGCGT    4140

CGGCGACCGC TACTGCCTGA TGCTGCACGC GAACGGCTTC ATCGACCCGC TCTTCTCCCG    4200

GGGGCTGGAA AACACCGCGG TGACCATCCA CGCGCTCGCG GCGCGCCTCA TCAAGGCGCT    4260

GCGCGACGAC GACTTCTCCC CCGAGCGCTT CGAGTACATC GAGCGCCTGC AGCAAAAGCT    4320

TTTGGACCAC AACGACGACT TCGTCAGCTG CTGCTACACG GCGTTCTCGG ACTTCCGCCT    4380

ATGGGACGCG TTCCACAGGC TGTGGGCGGT CGGCACCATC CTCGGGCAGT TCCGGCTCGT    4440

GCAGGCCCAC GCGAGGTTCC GCGCGTCGCG CAACGAGGGC GACCTCGATC ACCTCGACAA    4500
```

```
CGACCCTCCG TATCTCGGAT ACCTGTGCGC GGACATGGAG GAGTACTACC AGTTGTTCAA    4560

CGACGCCAAA GCCGAGGTCG AGGCCGTGAG TGCCGGGCGC AAGCCGGCCG ATGAGGCCGC    4620

GGCGCGGATT CACGCCCTCA TTGACGAACG AGACTTCGCC AAGCCGATGT TCGGCTTCGG    4680

GTACTGCATC ACCGGGGACA AGCCGCAGCT CAACAACTCG AAGTACAGCC TGCTGCCGGC    4740

GATGCGGCTG ATGTACTGGA CGCAAACCCG CGCGCCGGCA GAGGTGAAAA AGTACTTCGA    4800

CTACAACCCG ATGTTCGCGC TGCTCAAGGC GTACATCACG ACCCGCATCG GCCTGGCGCT    4860

GAAGAAGTAG CCGCTCGACG ACGACATAAA AACGATGAAC GACATTCAAT TGGATCAAGC    4920

GAGCGTCAAG AAGCGTCCCT CGGGCGCGTA CGACGCAACC ACGCGCCTGG CCGCGAGCTG    4980

GTACGTCGCG ATGCGCTCCA ACGAGCTCAA GGACAAGCCG ACCGAGTTGA CGCTCTTCGG    5040

CCGTCCGTGC GTGGCGTGGC GCGGAGCCAC GGGGCGGGCC GTGGTGATGG ACCGCCACTG    5100

CTCGCACCTG GGCGCGAACC TGGCTGACGG GCGGATCAAG GACGGGTGCA TCCAGTGCCC    5160

GTTTCACCAC TGGCGGTACG ACGAACAGGG CCAGTGCGTT CACATCCCCG GCCATAACCA    5220

GGCGGTGCGC CAGCTGGAGC CGGTGCCGCG CGGGGCGCGT CAGCCGACGT TGGTCACCGC    5280

CGAGCGATAC GGCTACGTGT GGGTCTGGTA CGGCTCCCCG CTGCCGCTGC ACCCGCTGCC    5340

CGAAATCTCC GCGGCCGATG TCGACAACGG CGACTTTATG CACCTGCACT TCGCGTTCGA    5400

GACGACCACG GCGGTCTTGC GGATCGTCGA GAACTTCTAC GACGCGCAGC ACGCAACCCC    5460

GGTGCACGCA CTCCCGATCT CGGCCTTCGA ACTCAAGCTC TTCGACGATT GGCGCCAGTG    5520

GCCGGAGGTT GAGTCGCTGG CCCTGGCGGG CGCGTGGTTC GGTGCCGGGA TCGACTTCAC    5580

CGTGGACCGG TACTTCGGCC CCCTCGGCAT GCTGTCACGC GCGCTCGGCC TGAACATGTC    5640

GCAGATGAAC CTGCACTTCG ATGGCTACCC CGGCGGGTGC GTCATGACCG TCGCCCTGGA    5700

CGGAGACGTC AAATACAAGC TGCTCCAGTG TGTGACGCCG GTGAGCGAAG GCAAGAACGT    5760

CATGCACATG CTCATCTCGA TCAAGAAGGT GGGCGGCATC CTGCGCCGCG CGACCGACTT    5820

CGTGCTGTTC GGGCTGCAGA CCAGGCAGGC CGCGGGGTAC GACGTCAAAA TCTGGAACGG    5880

AATGAAGCCG GACGGCGGCG GCGCGTACAG CAAGTACGAC AAGCTCGTGC TCAAGTACCG    5940

GGCGTTCTAT CGAGGCTGGG TCGACCGCGT CGCAAGTGAG CGGTGATGCG TGAAGCCGAG    6000

CCGCTCTCGA CCGCGTCGCT GCGCCAGGCG CTCGCGAACC TGGCGAGCGG CGTGACGATC    6060

ACGGCCTACG GCGCGCCGGG CCCGCTTGGG CTCGCGGCCA CCAGCTTCGT GTCGGAGTCG    6120

CTCTTTGCGA GGTATTCATG ACTATCTGGC TGTTGCAACT CGTGCTGGTG ATCGCGCTCT    6180

GCAACGTCTG CGGCCGCATT GCCGAACGGC TCGGCCAGTG CGCGGTCATC GGCGAGATCG    6240

CGGCCGGTTT GCTGTTGGGG CCGTCGCTGT TCGGCGTGAT CGCACCGAGT TTCTACGACC    6300

TGTTGTTCGG CCCCCAGGTG CTGTCAGCGA TGGCGCAAGT CAGCGAAGTC GGCCTGGTAC    6360

TGCTGATGTT CCAGGTCGGC CTGCATATGG AGTTGGGCGA GACGCTGCGC GACAAGCGCT    6420

GGCGCATGCC CGTCGCGATC GCAGCGGGCG GGCTCGTCGC ACCGGCCGCG ATCGGCATGA    6480

TCGTCGCCAT CGTTTCGAAA GGCACGCTCG CCAGCGACGC GCCGGCGCTG CCCTATGTGC    6540

TCTTCTGCGG TGTCGCACTT GCGGTATCGG CGGTGCCGGT GATGGCGCGC ATCATCGACG    6600

ACCTGGAGCT CAGCGCCATG GTGGGCGCGC GGCACGCAAT GTCTGCCGCG ATGCTGACGG    6660

ATGCGCTCGG ATGGATGCTG CTTGCAACGA TTGCCTCGCT ATCGAGCGGG CCCGGCTGGG    6720

CATTTGCGCG CATGCTCGTC AGCCTGCTCG CGTATCTGGT GCTGTGCGCG CTGCTGGTGC    6780

GCTTCGTGGT TCGACCGACC CTTGCGCGGC TCGCGTCGAC CGCGCATGCG ACGCGCGACC    6840

GCTTGGCCGT GTTGTTCTGC TTCGTAATGT TGTCGGCACT CGCGACGTCG CTGATCGGAT    6900
```

TCCATAGCGC TTTTGGCGCA CTTGCCGCGG CGCTGTTCGT GCGCCGGGTG CCCGGCGTCG     6960

CGAAGGAGTG GCGCGACAAC GTCGAAGGTT TCGTCAAGCT T                        7001

(2) INFORMATION FOR SEQ ID NO:7:

(i) SEQUENCE CHARACTERISTICS:
        (A) LENGTH: 1097 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: pKK223-3

(ix) FEATURE:
        (A) NAME/KEY: misc_feature
        (B) LOCATION: 1
        (D) OTHER INFORMATION: /note= "BssHII site"

(ix) FEATURE:
        (A) NAME/KEY: misc_feature
        (B) LOCATION: 7
        (D) OTHER INFORMATION: /note= "BglII site"

(ix) FEATURE:
        (A) NAME/KEY: misc_feature
        (B) LOCATION: 265
        (D) OTHER INFORMATION: /note= "EcoRI site"

(ix) FEATURE:
        (A) NAME/KEY: misc_feature
        (B) LOCATION: 270
        (D) OTHER INFORMATION: /note= "SmaI site"

(ix) FEATURE:
        (A) NAME/KEY: misc_feature
        (B) LOCATION: 275
        (D) OTHER INFORMATION: /note= "BamHI site"

(ix) FEATURE:
        (A) NAME/KEY: misc_feature
        (B) LOCATION: 281
        (D) OTHER INFORMATION: /note= "SalI site"

(ix) FEATURE:
        (A) NAME/KEY: misc_feature
        (B) LOCATION: 287
        (D) OTHER INFORMATION: /note= "PstI site"

(ix) FEATURE:
        (A) NAME/KEY: misc_feature
        (B) LOCATION: 293
        (D) OTHER INFORMATION: /note= "XbaI site"

(ix) FEATURE:
        (A) NAME/KEY: misc_feature
        (B) LOCATION: 299
        (D) OTHER INFORMATION: /note= "XhoI site"

(ix) FEATURE:
        (A) NAME/KEY: misc_feature
        (B) LOCATION: 305
        (D) OTHER INFORMATION: /note= "KpnI site"

(ix) FEATURE:
        (A) NAME/KEY: misc_feature
        (B) LOCATION: 311
        (D) OTHER INFORMATION: /note= "NotI site"

(ix) FEATURE:
        (A) NAME/KEY: misc_feature
        (B) LOCATION: 319
        (D) OTHER INFORMATION: /note= "HindIII site"

(ix) FEATURE:

(A) NAME/KEY: misc_feature
                (B) LOCATION: 1086
                (D) OTHER INFORMATION: /note= "BglI site"

(ix) FEATURE:
                (A) NAME/KEY: misc_feature
                (B) LOCATION: 1092
                (D) OTHER INFORMATION: /note= "BssHII site"

(ix) FEATURE:
                (A) NAME/KEY: promoter
                (B) LOCATION: 185..264
                (D) OTHER INFORMATION: /standard_name= "tac"

(ix) FEATURE:
                (A) NAME/KEY: terminator
                (B) LOCATION: 327..752
                (D) OTHER INFORMATION: /standard_name= "rrnB"

(xi) SEQUENCE DESCRIPTION: SEQ ID NO:7:

```
GCGCGCAGAT CTGGGCTTAT CGACTGCACG GTGCACCAAT GCTTCTGGCG TCAGGCAGCC        60

ATCGGAAGCT GTGGTATGGC TGTGCAGGTC GTAAATCACT GCATAATTCG TGTCGCTCAA       120

GGCGCACTCC CGTTCTGGAT AATGTTTTTT GCGCCGACAT CATAACGGTT CTGGCAAATA       180

TTCTGAAATG AGCTGTTGAC AATTAATCAT CGGCTCGTAT AATGTGTGGA ATTGTGAGCG       240

GATAACAATT TCACACAGGA AACAGAATTC CCGGGGATCC GTCGACCTGC AGTCTAGACT       300

CGAGGGTACC GCGGCCGCAA GCTTGGCTGT TTTGGCGGAT GAGAGAAGAT TTTCAGCCTG       360

ATACAGATTA AATCAGAACG CAGAAGCGGT CTGATAAAAC AGAATTTGCC TGGCGGCAGT       420

AGCGCGGTGG TCCCACCTGA CCCCATGCCG AACTCAGAAG TGAAACGCCG TAGCGCCGAT       480

GGTAGTGTGG GGTCTCCCCA TGCGAGAGTA GGGAACTGCC AGGCATCAAA TAAAACGAAA       540

GGCTCAGTCG AAAGACTGGG CCTTTCGTTT TATCTGTTGT TTGTCGGTGA ACGCTCTCCT       600

GAGTAGGACA AATCCGCCGG GAGCGGATTT GAACGTTGCG AAGCAACGGC CCGGAGGGTG       660

GCGGGCAGGA CGCCCGCCAT AAACTGCCAG GCATCAAATT AAGCAGAAGG CCATCCTGAC       720

GGATGGCCTT TTTGCGTTTC TACAAACTCT TTTGTTTATT TTTCTAAATA CATTCAAATA       780

TGTATCCGCT CATGAGACAA TAACCCTGAT AAATGCTTCA ATAATATTGA AAAGGAAGA       840

GTATGAGTAT TCAACATTTC CGTGTCGCCC TTATTCCCTT TTTTGCGGCA TTTTGCCTTC       900

CTGTTTTTGC TCACCCAGAA ACGCTGGTGA AAGTAAAAGA TGCTGAAGAT CAGTTGGGTG       960

CACGAGTGGG TTACATCGAA CTGGATCTCA ACAGCGGTAA GATCCTTGAG AGTTTTCGCC      1020

CCGAAGAACG TTTTCCAATG ATGAGCACTT TTAAAGTTCT GCTATGTGGC GCGGTATTAT      1080

CCCGTAGATC TGCGCGC                                                     1097
```

(2) INFORMATION FOR SEQ ID NO:8:

(i) SEQUENCE CHARACTERISTICS:
                (A) LENGTH: 3186 base pairs
                (B) TYPE: nucleic acid
                (C) STRANDEDNESS: single
                (D) TOPOLOGY: linear (ii) MOLECULE TYPE: DNA (genomic)

(iii) HYPOTHETICAL: NO (iv) ANTI-SENSE: NO (vi) ORIGINAL SOURCE:
                (A) ORGANISM: Pseudomonas fluorescens
                (B) STRAIN: CGA267356 (aka MOCG134 and aka BL915)

(vii) IMMEDIATE SOURCE:
                (B) CLONE: pCIB146

(ix) FEATURE:
  (A) NAME/KEY: RBS
  (B) LOCATION: 245..251
  (D) OTHER INFORMATION: /note= "potential ribosome binding site"

(ix) FEATURE:
  (A) NAME/KEY: misc_feature
  (B) LOCATION: 256..3006
  (D) OTHER INFORMATION: /product= "LemA"
      /note= "LemA coding sequence."

(xi) SEQUENCE DESCRIPTION: SEQ ID NO:8:

```
GATCCGGGGA TGGCCGGCAG ATACGGGATT CATTGGCTTC TGCAAGTAAT TCTCAGTTGC      60

GCGATTATTC AAGATTGTCC GCGGCCGGGC AACCGACACC GGTCGACAAA ACGCTGGCCG     120

GGCGCCGAGA CATCCGAGCC ATTGCGCGGT CAATTTTGCG AAGAATGCCG TCAAGCAAAT     180

GGCTACACTG CGCAGGTGGT GCGCACCGGA CGTGCGCAGG GTTCATTCAA AATGGCGTGG     240

TAGCAGGAGA GTTGCGTGCT TAAGAAACTG GGAATCAAAG GCCGCGTGCT GTTACTGACC     300

TTGCTGCCAA CCAGCCTGAT GGCGTTGGTA CTGGGCGGTT ATTTCACCTG GATGCAGCAA     360

TCGGACCTGC AAACCCAGCT TCTGCACCGC GGCGAAATGA TCGCCGAGCA ACTGGCGCCC     420

CTGGTGGCTC CCGCCCTGGC CCACCAGGAC ACTTCCCTGC TGGAGCGCAT CGCCACCCAA     480

TCCCTGGAAC AGCAGGACGT GCGCGCAGTG ACTTTCCTCG CGCCCGACCG CACGCCGCTG     540

GCCCATGCCG GCCCGAGCAT GCTCAACCAG GCGCCGACCG GCAACGGCAG CCAGCTGCTG     600

CAACGCACCG GCAGCGACGC CACCCGCTAT CTGCTGCCGG TATTCGGCCG CCACCGCAAC     660

CTGGCCGGCG ACCTGATTCC CGACGAGTCC GACCGCCTGC TCGGCTGGGT CGAGCTGGAA     720

CTGTCCCATA ACAGCATGCT GCTGCGCGGC TACCGCAGCC TGTTCGCCAG CCTGCTGCTG     780

ATTACCGCCG GGCTGATCTG CACCGGCCTG CTGGCACTGC GCATGGGGCG AACCATCAAC     840

GACCCGCTGA GCCAGATCAA ACAGGCCGTC ACCCAGCTCA AGGACGGCAA CCTGGAAACC     900

CGCCTGCCCT TGCTCGGCAG CCAGGAACTG GACGAGCTGG CCTCGGGCAT CAACCGCATG     960

GCCGGCACCC TGCAGAATGC CCAGGAAGAA CTGCAGCACA GCATCGACCA GGCCACCGAG    1020

GACGTCCGGC AAAACCTGGA GACCATCGAG ATCCAGAACA TCGAGCTGGA CCTGGCGCGC    1080

AAGGAGGCCC TGGAGGCCAG CCGGATCAAG TCCGAATTCC TGGCCAACAT GAGCCATGAA    1140

ATCCGCACGC CGCTCAACGG CATCCTCGGC TTCACTCATT TGTTGCAGAA AAGCGAGCTG    1200

ACCCCGCGCC AGCTGGATTA CCTGGGCACC ATCGAAAAAT CCGCCGACAG CCTGCTGGGA    1260

ATCATCAACG AAATTCTCGA CTTCTCGAAA ATCGAAGCCG GCAAGCTGGT GCTCGACAGC    1320

ATTCCGTTCA ACCTGCGCGA CCTGTTGCAG GACACCCTGA CCATTCTCGC TCCGGCCGCC    1380

CACGCCAAGC AGCTGGAACT GGTCAGCCTG GTGTATCGCG ATAGCCCGCT GTCGCTGGTG    1440

GGCGACCCGC TGCGCCTCAA GCAGATCCTC ACCAATCTGG TGAGCAACGC CATCAAGTTC    1500

ACCCGCGAAG GCACCATCGT CGCCCGGGCC ATGCTTGAAG AGGAGCACGA AGACAGCGTG    1560

CAACTGCGCA TCAGCATTCA GGACACCGGC ATCGGCCTGT CGAACCAGGA CGTGCGCGCC    1620

CTGTTCCAGG CGTTCAGCCA GGCCGACAAT TCGCTGTCGC GACAACCCGG CGGGACTGGC    1680

CTGGGGCTGG TGATTTCCAA GCGCCTGATC GAACAGATGG GCGGCGAGAT CGGCGTCGAC    1740

AGCACGCCCG GCGAAGGTTC GGAGTTCTGG ATCAGCCTGC GCCTGCCGAA AACCCGCGAC    1800

GACGCCGAAG ACCTGCCGGC CCCGCCGCTG CTCGGCAGGC GGGTCGCGGT CCTGGAAAAC    1860

CATGAGCTGG CGCGCCAGGC CCTGCAGCAT CAACTCGAGG ACTGCGGCCT GGAAGTCACT    1920

CCGTTCAACA CCCTGGAAGC CCTGACCAAC GGGGTGACCG GCGTGCACCA GACCGACCAG    1980
```

```
GCGATCGATC TGGCGGTCCT CGGCATCACC ACCAACGACA TGCTGCCGGA ACGCCTCAAC    2040

CAGCACATCT GGGACCTCGA GCACCTGGGC TGCAAAGTCC TGGTGCTGTG CCCGACCACA    2100

GAACAGACAC TCTTCCACCT GTCGGTGCCC AACCCTCACA GCCAGTTGCA GGCCAAACCG    2160

GCGTGCACGC GCAAACTGCG GCGCGCCCTG GCCGACCTGG TCAACCCCAA GGTGGTGCGC    2220

AGCGAGCCGA GCGAACCGAT CGCCAGCCGC CCGCCACGGG TGCTGTGTGT CGATGACAAC    2280

CCGGCCAACC TGCTGCTGGT GCAGACCCTG CTCGAAGACA TGGGCGCCAA AGTGCTCGCG    2340

GTCGACAGCG GCTATGCGGC GGTCAAGGCG GTGCAGAGCG AGTCGTTCGA CCTGGTGATG    2400

ATGGACGTGC AGATGCCCGG CATGGACGGT CGCCAGAGCA CCGAGGCGAT TCGCCAGTGG    2460

GAAAGCGGGC GCAACTGCTC GCCGCTGCCG GTGATCGCCC TCACCGCCCA CGCCATGGCC    2520

AACGAAAAAC GCGCGCTGCT GCAAAGCGGC ATGGACGATT ACCTGACCAA ACCCATCAGT    2580

GAGCGGCAAC TGGCCCAGGT GGTGCTGAAG TGGACCGGCC TGGCCCTGCG CAACCAAGGT    2640

CCGGAACGCT CTGGCGAAGT GTCTGGCAAC GGCCTCGAGC TGCAAGTGCT GGATCACGAC    2700

GAAGGCTTGC TCCTGGCCGC CGGCAAGGCG GACCTGGCGG CCGACATGCT GGCCATGCTC    2760

CTGGCCTCGC TGGAAGCCGA TCGCGAAGCG ATTCGCGCCG CCCGTGCCGC CAACGATCAC    2820

AATGCGTTGA TCGAGCGGGT CCATCGCCTG CACGGGGCGA CCCGCTATTG TGGCGTGCCG    2880

CAGTTGCGCG CCGCCTGCCA GCGCAGCGAA ACCCTGCTCA GCAGGAAGA CGTCAAGGCC    2940

TTCGCCGCCC TCGACGAGCT CGAACGGGCC ATTAGTCGCC TGGCCACGGA GGCCCGCATC    3000

AACGCCTGAT TCAAGGCAAC GACACGTCAG CCCCGCAGGT TCATGCTCGG GGCAACTTTC    3060

ACAAGGACGA CGCCATGCGC ACGATTCTCT TCAGCAGCCA GAACTATGAC CGCGACAGCT    3120

TCCTCGGCGC CGCCCTGCCG CCGGGCATCG AGCTGCAATT CCAGGCGGCG CGCCTGAGCC    3180

TGGACA                                                               3186
```

(2) INFORMATION FOR SEQ ID NO:9:

(i) SEQUENCE CHARACTERISTICS:
        (A) LENGTH: 642 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: CGA375260

(ix) FEATURE:
        (A) NAME/KEY: CDS
        (B) LOCATION: 1..639
        (D) OTHER INFORMATION: /product= "gac*3 gene"
        (D) OTHER INFORMATION: /transl_except= (pos: 1 .. 3, aa: Met (xi) SEQUENCE DESCRIPTION: SEQ ID NO:9:

```
TTG ATT AGG GTG CTA GTA GTC GAT GAC CAT GAT CTC GTT CGT ACA GGT       48
Met Ile Arg Val Leu Val Val Asp Asp His Asp Leu Val Arg Thr Gly
 1               5                  10                  15

ATT ACA CGA ATG CTG GCT GAC ATC GAT GGC CTG CAA GTG GTC GGC CAG       96
Ile Thr Arg Met Leu Ala Asp Ile Asp Gly Leu Gln Val Val Gly Gln
            20                  25                  30

GCC GAG TCA GGG GAG GAA TCC CTG CTC AAG GCC CGG GAG TTG AAA CCC      144
Ala Glu Ser Gly Glu Glu Ser Leu Leu Lys Ala Arg Glu Leu Lys Pro
        35                  40                  45
```

```
GAT GTG GTC CTC ATG GAC GTC AAG ATG CCC GGG ATC GGC GGT CTT GAA        192
Asp Val Val Leu Met Asp Val Lys Met Pro Gly Ile Gly Gly Leu Glu
    50                  55                  60

GCC ACG CGC AAA TTG TTG CGC AGT CAC CCG GAT ATC AAA GTC GTG GCC        240
Ala Thr Arg Lys Leu Leu Arg Ser His Pro Asp Ile Lys Val Val Ala
65                  70                  75                  80

GTC ACC GTG TGT GAA GAA GAT CCG TTC CCG ACC CGC TTG CTG CAA GCC        288
Val Thr Val Cys Glu Glu Asp Pro Phe Pro Thr Arg Leu Leu Gln Ala
                85                  90                  95

GGC GCG GCG GGT TAC CTG ACC AAG GGG GCG GGC CTC AAT GAA ATG GTG        336
Gly Ala Ala Gly Tyr Leu Thr Lys Gly Ala Gly Leu Asn Glu Met Val
            100                 105                 110

CAG GCC ATT CGC CTG GTG TTT GCC GGC CAG CGT TAC ATC AGC CCG CAA        384
Gln Ala Ile Arg Leu Val Phe Ala Gly Gln Arg Tyr Ile Ser Pro Gln
        115                 120                 125

ATT GCC CAG CGG TTG GTG TTC AAG TCA TTC CAG CCT TCC AGT GAT TCA        432
Ile Ala Gln Arg Leu Val Phe Lys Ser Phe Gln Pro Ser Ser Asp Ser
130                 135                 140

CCG TTC GAT GCT TTG TCC GAG CGG GAA ATC CAG ATC GCG CTG ATG ATT        480
Pro Phe Asp Ala Leu Ser Glu Arg Glu Ile Gln Ile Ala Leu Met Ile
145                 150                 155                 160

GTC GGC TGC CAG AAA GTG CAG ATC ATC TCC GAC AAG CTG TGC CTG TCT        528
Val Gly Cys Gln Lys Val Gln Ile Ile Ser Asp Lys Leu Cys Leu Ser
                165                 170                 175

CCG AAA ACC GTT AAT ACC TAC CGT TAC CGC ATC TTC GAA AAG CTC TCG        576
Pro Lys Thr Val Asn Thr Tyr Arg Tyr Arg Ile Phe Glu Lys Leu Ser
            180                 185                 190

ATC AGC AGC GAT GTT GAA CTG ACA TTG CTG GCG GTT CGC CAC GGC ATG        624
Ile Ser Ser Asp Val Glu Leu Thr Leu Leu Ala Val Arg His Gly Met
        195                 200                 205

GTC GAT GCC AGT GCC TGA                                                642
Val Asp Ala Ser Ala
    210
```

(2) INFORMATION FOR SEQ ID NO:10:

(i) SEQUENCE CHARACTERISTICS:
        (A) LENGTH: 213 amino acids
        (B) TYPE: amino acid
        (D) TOPOLOGY: linear (ii) MOLECULE TYPE: protein (xi) SEQUENCE DESCRIPTION: SEQ ID NO:10:

```
Met Ile Arg Val Leu Val Asp Asp His Asp Leu Val Arg Thr Gly
1               5                   10                  15

Ile Thr Arg Met Leu Ala Asp Ile Asp Gly Leu Gln Val Gly Gln
                20                  25                  30

Ala Glu Ser Gly Glu Glu Ser Leu Leu Lys Ala Arg Glu Leu Lys Pro
        35                  40                  45

Asp Val Val Leu Met Asp Val Lys Met Pro Gly Ile Gly Gly Leu Glu
    50                  55                  60

Ala Thr Arg Lys Leu Leu Arg Ser His Pro Asp Ile Lys Val Val Ala
65                  70                  75                  80

Val Thr Val Cys Glu Glu Asp Pro Phe Pro Thr Arg Leu Leu Gln Ala
                85                  90                  95

Gly Ala Ala Gly Tyr Leu Thr Lys Gly Ala Gly Leu Asn Glu Met Val
            100                 105                 110

Gln Ala Ile Arg Leu Val Phe Ala Gly Gln Arg Tyr Ile Ser Pro Gln
        115                 120                 125
```

-continued

```
Ile Ala Gln Arg Leu Val Phe Lys Ser Phe Gln Pro Ser Ser Asp Ser
    130                 135                 140

Pro Phe Asp Ala Leu Ser Glu Arg Glu Ile Gln Ile Ala Leu Met Ile
145                 150                 155                 160

Val Gly Cys Gln Lys Val Gln Ile Ile Ser Asp Lys Leu Cys Leu Ser
                165                 170                 175

Pro Lys Thr Val Asn Thr Tyr Arg Tyr Arg Ile Phe Glu Lys Leu Ser
            180                 185                 190

Ile Ser Ser Asp Val Glu Leu Thr Leu Leu Ala Val Arg His Gly Met
        195                 200                 205

Val Asp Ala Ser Ala
    210
```

(2) INFORMATION FOR SEQ ID NO:11:

(i) SEQUENCE CHARACTERISTICS:
        (A) LENGTH: 5698 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Pseudomonas aureofaciens
        (B) STRAIN: 30-84

(vii) IMMEDIATE SOURCE:
        (B) CLONE: phzFABCD (ix) FEATURE:
        (A) NAME/KEY: misc_feature
        (B) LOCATION: 105..1307
        (D) OTHER INFORMATION: /product= "phzF"
           /note= "ORF1"

(ix) FEATURE:
        (A) NAME/KEY: misc_feature
        (B) LOCATION: 1323..1946
        (D) OTHER INFORMATION: /product= "phzA"
           /note= "ORF2"

(ix) FEATURE:
        (A) NAME/KEY: misc_feature
        (B) LOCATION: 1943..3856
        (D) OTHER INFORMATION: /product= "phzB"
           /note= "ORF3"

(ix) FEATURE:
        (A) NAME/KEY: misc_feature
        (B) LOCATION: 3859..4695
        (D) OTHER INFORMATION: /product= "phzC"
           /note= "ORF4"

(ix) FEATURE:
        (A) NAME/KEY: misc_feature
        (B) LOCATION: 4692..5360
        (D) OTHER INFORMATION: /product= "phzD"
           /note= "ORF5"

(xi) SEQUENCE DESCRIPTION: SEQ ID NO:11:

```
GAATTCATGA ACGTCTTTCA GCAACTGCGC GCCCTGGGTA TTCCAGTACC GCAAATCAAG        60

CGCGAAGGCA TTCCAACTTA ATCCCTCGTG AGAGTGATCG CATCATGGAA GACTTACTGA       120

AACGGGTTTT AAGTTGTGAA GCGTTCCAGC AGCCTCAATG GAGCGAGCCC TCACAATTGC       180

ATGACGCGCA GGCCTACCTC AGGGACAGCG CCTCATTGAT ACGAGTGGAA GACATCCTGG       240
```

```
TGCTGCGCGC CACGCTGGCG CGTGTAGCGG CCGGCGAAGC AATGGTCATC CAGTCCGGTG    300

ACTGCGCCGA GGACATGGAT GAAAGCACTC CCGACCATGT GGCCCGCAAA GCCGCGGTAC    360

TGGACATCCT GGCCGGTACG TTCCGGCTGG TGACCCAACA ACCGGTGGTA CGGGTGGGAC    420

GAATTGCCGG GCAGTTTGCC AAGCCGCGTT CCAACAACAA CGAACGCATC GGCGATGTCG    480

AATTACCGGT GTATCGCGGC GACATGGTCA ACGGTCGCGA GGCCGTCTGC GGTCATCGCC    540

AGCACGATGC GCAACGCCTG GTTCGAGGCT ATAGCGCCGC GCGGGACATC ATGCAACACC    600

TGGGCTGGAA AGCCTCGGCA AGCCAGGAAC AACTCAGCGG TTCACCGGCC TGGACCAACC    660

ATGAAATGCT GGTACTCGAC TACGAACTGC CACAACTGCG CCAGGACGAA CAGGGCCGGG    720

TATTTCTCGG TTCTACCCAC TGGCCGTGGA TCGGCGAGCG TACCCGTCAG TTAACGGGCG    780

CTCACGTGAC GCTGCTCAGC GAAGTGCTCA ATCCGGTGGC GTGCAAGGTC GGCCCGGACA    840

TTACCCAAGA CCAGTTACTG AGCCTGTGTG AACGCCTGGA CGCCAAGCGC GAACCCGGCC    900

GGCTGACCCT GATTGCCCGC ATGGGCGCGC AAAAGGTCGC CGAGCGCCTG CCGCCGCTGG    960

TCGAAGCGGT GCGCCAGGCC GGCCACAAGA TCATCTGGCT GAGCGACCCG ATGCACGGCA   1020

ACACCATCGT CGCGCCCTGC GGCAACAAGA CCCGCATGGT GCAGGCCATC ACCGAGGAAA   1080

TCGCCGCCTT CAAGCATGCC GTGACCTCCG CCGGTGGCGT GGCCGCCGGC CTGCACCTGG   1140

AAACCACCCC TGACGACGTC AGCGAGTGCG CTTCCGATGC CGCCGGCCTG CATCAGGTCG   1200

CCAGCCGCTA CAAAAGCCTG TGCGACCCGC GCCTGAACCC CTGGCAAGCC ATTACTGCGG   1260

TGATGGCCTG GAAAAACCAG CCCTCTTCAA CCCTTGCCTC CTTTTGACTG GAGTTTGTCG   1320

TCATGACCGG CATTCCATCG ATCGTCCCTT ACGCCTTGCC TACCAACCGC GACCTGCCCG   1380

TCAACCTCGC GCAATGGAGC ATCGACCCCG AGCGTGCCGT GCTGCTGGTG CATGACATGC   1440

AGCGCTACTT CCTGCGGCCC TTGCCCGACG CCCTGCGTGA CGAAGTCGTG AGCAATGCCG   1500

CGCGCATTCG CCAGTGGGCT GCCGACAACG GCGTTCCGGT GGCCTACACC GCCCAGCCCG   1560

GCAGCATGAG CGAGGAGCAA CGCGGGCTGC TCAAGGACTT CTGGGGCCCG GGCATGAAGG   1620

CCAGCCCCGC CGACCGCGAG GTGGTCGGCG CCCTGACGCC CAAGCCCGGC GACTGGCTGC   1680

TGACCAAGTG GCGCTACAGC GCGTTCTTCA ACTCCGACCT GCTGGAACGC ATGCGCGCCA   1740

ACGGGCGCGA TCAGTTGATC CTGTGCGGGG TGTACGCCCA TGTCGGGGTA CTGATTTCCA   1800

CCGTGGATGC CTACTCCAAC GATATCCAGC CGTTCCTCGT TGCCGACGCG ATCGCCGACT   1860

TCAGCAAAGA GCACCACTGG ATGGCCATCG AATACGCCGC CAGCCGTTGC GCCATGGTCA   1920

TCACCACCGA CGAGGTGGTG CTATGAGCCA GACCGCAGCC CACCTCATGG AACGCATCCT   1980

GCAACCGGCT CCCGAGCCGT TTGCCCTGTT GTACCGCCCG GAATCCAGTG GCCCCGGCCT   2040

GCTGGACGTG CTGATCGGCG AAATGTCGGA ACCGCAGGTC CTGGCCGATA TCGACTTGCC   2100

TGCCACCTCG ATCGGCGCGC CTCGCCTGGA TGTACTGGCG CTGATCCCCT ACCGCCAGAT   2160

CGCCGAACGC GGTTTCGAGG CGGTGGACGA TGAGTCGCCG CTGCTGGCGA TGAACATCAC   2220

CGAGCAGCAA TCCATCAGCA TCGAGCGCTT GCTGGGAATG CTGCCCAACG TGCCGATCCA   2280

GTTGAACAGC GAACGCTTCG ACCTCAGCGA CGCGAGCTAC GCCGAGATCG TCAGCCAGGT   2340

GATCGCCAAT GAAATCGGCT CCGGGGAAGG CGCCAACTTC GTCATCAAAC GCACCTTCCT   2400

GGCCGAGATC AGCGAATACG GCCCGGCCAG TGCGCTGTCG TTCTTTCGCC ATCTGCTGGA   2460

ACGGGAGAAA GGCGCCTACT GGACGTTCAT CATCCACACC GGCAGCCGTA CCTTCGTGGG   2520

TGCGTCCCCC GAGCGCCACA TCAGCATCAA GGATGGGCTC TCGGTGATGA ACCCCATCAG   2580

CGGCACTTAC CGCTATCCGC CCGCCGGCCC CAACCTGTCG GAAGTCATGG ACTTCCTGGC   2640
```

```
GGATCGCAAG GAAGCCGACG AGCTCTACAT GGTGGTGGAT GAAGAGCTGA AAATGATGGC    2700

GCGCATTTGT GAGGACGGCG GCCACGTCCT CGGCCCTTAC CTCAAGGAAA TGGCGCACCT    2760

GGCCCACACC GAGTACTTCA TCGAAGGCAA GACCCATCGC GATGTACGGG AAATCCTGCG    2820

CGAAACCCTG TTTGCGCCCA CCGTCACCGG CAGCCCACTG GAAAGCGCCT GCCGGGTCAT    2880

CCAGCGCTAT GAGCCGCAAG GCCGCGCGTA CTACAGCGGC ATGGCTGCGC TGATCGGCAG    2940

CGATGGCAAG GGCGGGCGTT CCCTGGACTC CGCGATCCTG ATTCGTACCG CCGACATCGA    3000

TAACAGCGGC GAGGTGCGGA TCAGCGTGGG CTCGACCATC GTGCGCCATT CCGACCCGAT    3060

GACCGAGGCT GCCGAAAGCC GGGCCAAGGC CACTGGCCTG ATCAGCGCAC TGAAAAACCA    3120

GGCGCCCTCG CGCTTCGGCA ATCACCTGCA AGTGCGCGCC GCATTGGCCA GCCGCAATGC    3180

CTACGTCTCG GACTTCTGGC TGATGGACAG CCAGCAGCGG GAGCAGATCC AGGCCGACTT    3240

CAGTGGGCGC CAGGTGCTGA TCGTCGACGC CGAAGACACC TTCACCTCGA TGATCGCCAA    3300

GCAACTGCGG GCCCTGGGCC TGGTAGTGAC GGTGTGCAGC TTCAGCGACG AATACAGCTT    3360

TGAAGGCTAC GACCTGGTCA TCATGGGCCC CGGCCCCGGC AACCCGAGCG AAGTCCAACA    3420

GCCGAAAATC AACCACCTGC ACGTGGCCAT CCGCTCCTTG CTCAGCCAGC AGCGGCCATT    3480

CCTCGCGGTG TGCCTGAGCC ATCAGGTGCT GAGCCTGTGC CTGGGCCTGG AACTGCAGCG    3540

CAAAGCCATT CCCAACCAGG GCGTGCAAAA ACAGATCGAC CTGTTTGGCA ATGTCGAACG    3600

GGTGGGTTTC TACAACACCT TCGCCGCCCA GAGCTCGAGT GACCGCCTGG ACATCGACGG    3660

CATCGGCACC GTCGAAATCA GCCGCGACAG CGAGACCGGC GAGGTGCATG CCCTGCGTGG    3720

CCCCTCGTTC GCCTCCATGC AGTTTCATGC CGAGTCGCTG CTGACCCAGG AAGGTCCGCG    3780

CATCATCGCC GACCTGCTGC GGCACGCCCT GATCCACACA CCTGTCGAGA CAACGCTTC    3840

GGCCGCCGGG AGATAACCAT GGAGCATTAC GTCATCATCG ACGCCTTTGC CAGCGTCCCG    3900

CTGGAAGGCA ATCCGGTCGC GGTGTTCTTT GACGCCGATG ACTTGTCGGC CGAGCAAATG    3960

CAACGCATTG CCCGGGAGAT GAACCTGTCG GAAACCACTT TCGTGCTCAA GCCACGTAAC    4020

TGCGGCGATG CGCTGATCCG GATCTTCACC CCGGTCAACG AACTGCCCTT CGCCGGGCAC    4080

CCGTTGCTGG GCACGGACAT TGCCCTGGGT GCGCGCACCG ACAATCACCG GCTGTTCCTG    4140

GAAACCCAGA TGGGCACCAT CGCCTTTGAG CTGGAGCGCC AGAACGGCAG CGTCATCGCC    4200

GCCAGCATGG ACCAGCCGAT ACCGACCTGG ACGGCCCTGG GGCGCGACGC CGAGTTGCTC    4260

AAGGCCCTGG GCATCAGCGA CTCGACCTTT CCCATCGAGA TCTATCACAA CGGCCCGCGT    4320

CATGTGTTTG TCGGCCTGCC AAGCATCGCC GCGCTGTCGG CCCTGCACCC CGACCACCGT    4380

GCCCTGTACA GCTTCCACGA CATGGCCATC AACTGTTTTG CCGGTGCGGG ACGGCGCTGG    4440

CGCAGCCGGA TGTTCTCGCC GGCCTATGGG GTGGTCGAGG ATGCGGCCAC GGGCTCCGCT    4500

GCCGGGCCCT TGGCGATCCA TCTGGCGCGG CATGGCCAGA TCGAGTTCGG CCAGCAGATC    4560

GAAATTCTTC AGGGCGTGGA AATCGGCCGC CCCTCACTCA TGTTCGCCCG GGCCGAGGGC    4620

CGCGCCGATC AACTGACGCG GGTCGAAGTA TCAGGCAATG GCATCACCTT CGGACGGGGG    4680

ACCATCGTTC TATGAACAGT TCAGTACTAG GCAAGCCGCT GTTGGGTAAA GGCATGTCGG    4740

AATCGCTGAC CGGCACACTG GATGCGCCGT TCCCCGAGTA CCAGAAGCCG CCTGCCGATC    4800

CCATGAGCGT GCTGCACAAC TGGCTCGAAC GCGCACGCCG CGTGGGCATC CGCGAACCCC    4860

GTGCGCTGGC GCTGGCCACG GCTGACAGCC AGGGCCGGCC TTCGCACACGC ATCGTGGTGA    4920

TCAGTGAGAT CAGTGACACC GGGGTGCTGT TCAGCACCCA TGCCGGAAGC CAGAAAGGCC    4980

GCGAACTGAC AGAGAACCCC TGGGCCTCGG GGACGCTGTA TTGGCGCGAA ACCAGCCAGC    5040
```

```
AGATCATCCT CAATGGCCAG GCCGTGCGCA TGCCGGATGC CAAGGCTGAC GAGGCCTGGT    5100

TGAAGCGCCC TTATGCCACG CATCCGATGT CATCGGTGTC TCGCCAGAGT GAAGAACTCA    5160

AGGATGTTCA AGCCATGCGC AACGCCGCCA GGGAACTGGC CGAGGTTCAA GGTCCGCTGC    5220

CGCGTCCCGA GGGTTATTGC GTGTTTGAGT TACGGCTTGA ATCGCTGGAG TTCTGGGGTA    5280

ACGGCGAGGA GCGCCTGCAT GAACGCTTGC GCTATGACCG CAGCGCTGAA GGCTGGAAAC    5340

ATCGCCGGTT ACAGCCATAG GGTCCCGCGA TAAACATGCT TTGAAGTGCC TGGCTGCTCC    5400

AGCTTCGAAC TCATTGCGCA AACTTCAACA CTTATGACAC CCGGTCAACA TGAGAAAAGT    5460

CCAGATGCGA AAGAACGCGT ATTCGAAATA CCAAACAGAG AGTCCGGATC ACCAAAGTGT    5520

GTAACGACAT TAACTCCTAT CTGAATTTTA TAGTTGCTCT AGAACGTTGT CCTTGACCCA    5580

GCGATAGACA TCGGGCCAGA ACCTACATAA ACAAAGTCAG ACATTACTGA GGCTGCTACC    5640

ATGCTAGATT TTCAAAACAA GCGTAAATAT CTGAAAAGTG CAGAATCCTT CAAAGCTT     5698
```

What is claimed is:

1. A biocontrol strain of *Pseudomonas fluorescens* selected front the group consisting of: CGA364474, CGA364475, CGA366259, CGA376150, NOA402208, NOA402210, NOA402212, NOA402214, NOA402216, NOA409063, NOA409068, NOA413174, NOA413175, NOA413176, NOA413177, NOA413178; or pyrrolnitrin producing progeny thereof.

2. A method for controlling or inhibiting the growth of a plant pathogenic fungus by applying an effective amount of the biocontrol strain of claim 1 to an environment in which the plant pathogenic fungus may grow.

3. A method for controlling or inhibiting the growth of a plant pathogenic fungus by applying an effective amount of the biocontrol strain of claim 1 to a plant or plant part in order to protect said plant or plant part from a plant pathogenic fungus.

4. A method for controlling or inhibiting the growth of a plant pathogenic fungus by applying an effective amount of the biocontrol strain of claim 1 to seed in order to protect a plant that develops from said seed from a plant pathogenic fungus.

5. The method of claim 2, wherein said plant pathogenic fungus is Rhizoctonia or Pythium.

6. The method of claim 3, wherein said plant pathogenic fungus is Rhizoctonia or Pythium.

7. The method of claim 4, wherein said plant pathogenic fungus is Rhizoctonia or Pythium.

8. A biocontrol composition comprising the biocontrol strain of claim 1 in combination with a chemical fungicide.

9. The biocontrol composition of claim 8, wherein said chemical fungicide is a metalaxyl compound.

10. A method for controlling or inhibiting the growth of a plant pathogenic fungus by applying an effective amount of the biocontrol composition of claim 8 to an environment in which the plant pathogenic fungus may grow.

11. A method for controlling or inhibiting the growth of a plant pathogenic fungus by applying an effective amount of the biocontrol composition of claim 8 to a plant or plant part in order to protect said plant or plant part from a plant pathogenic fungus.

12. A method for controlling or inhibiting the growth of a plant pathogenic fungus by applying an effective amount of the biocontrol composition of claim 8 to seed in order to protect a plant that develops from said seed from a plant pathogenic fungus.

13. A biocontrol strain of *Pseudomonas fluorescens* according to claim 1, which is CGA364474 or pyrrolnitrin producing progeny thereof.

14. A biocontrol strain of *Pseudomonas fluorescens* according to claim 1, which is CGA364475 or pyrrolnitrin producing progeny thereof.

15. A biocontrol strain or *Pseudomonas fluorescens* according to claim 1, which is CGA366259 or pyrrolnitrin producing progeny thereof.

16. A biocontrol strain of *Pseudomonas fluorescens* according to claim 1, which is CGA376150 or pyrrolnitrin producing progeny thereof.

17. A biocontrol strain of *Pseudomonas fluorescens* according to claim 1, which is NOA402208 or pyrrolnitrin producing progeny thereof.

18. A biocontrol strain of *Pseudomonas fluorescens* according to claim 1, which is NOA402210 or pyrrolnitrin producing progeny thereof.

19. A biocontrol strain of *Pseudomonas fluorescens* according to claim 1, which is NOA402212 or pyrrolnitrin producing progeny thereof.

20. A biocontrol strain of *Pseudomonas fluorescens* according to claim 1, which is NOA402214 or pyrrolnitrin producing progeny thereof.

21. A biocontrol strain of *Pseudomonas fluorescens* according to claim 1, which is NOA402216 or pyrrolnitrin producing progeny thereof.

22. A biocontrol strain of *Pseudomonas fluorescens* according to claim 1, which is NOA409063 or pyrrolnitrin producing progeny thereof.

23. A biocontrol strain of *Pseudomonas fluorescens* according to claim 1, which is NOA409068 or pyrrolnitrin producing progeny thereof.

24. A biocontrol strain of *Pseudomonas fluorescens* according to claim 1, which is NOA413174 or pyrrolnitrin producing progeny thereof.

25. A biocontrol strain of *Pseudomonas fluorescens* according to claim 1, which is NOA413175 or pyrrolnitrin producing progeny thereof.

26. A biocontrol strain of *Pseudomonas fluorescens* according to claim 1, which is NOA413176 or pyrrolnitrin producing progeny thereof.

27. A biocontrol strain of *Pseudomonas fluorescens* according to claim 1, which is NOA413177 or pyrrolnitrin producing progeny thereof.

28. A biocontrol strain of *Pseudomonas fluorescens* according to claim 1, which is NOA413178 or pyrrolnitrin producing progeny thereof.

* * * * *